US012760117B2

(12) United States Patent
Shen et al.

(10) Patent No.: US 12,760,117 B2
(45) Date of Patent: Oct. 13, 2026

(54) NANOBODY TARGET MSLN AND USES IN CHIMERIC ANTIGEN RECEPTOR CELL THERAPY

(71) Applicants: Innovative Cellular Therapeutics Holdings, Ltd., Grand Cayman (KY); Innovative Cellular Therapeutics, Inc., Rockville, MD (US)

(72) Inventors: Xiaogang Shen, Shanghai (CN); Wensheng Wang, Shanghai (CN); Xudong Tang, Shanghai (CN); Chengfei Pu, Shanghai (CN); Zhao Wu, Shanghai (CN); Lei Xiao, Rockville, MD (US)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 469 days.

(21) Appl. No.: 18/540,269

(22) Filed: Dec. 14, 2023

(65) Prior Publication Data

US 2024/0199760 A1 Jun. 20, 2024

Related U.S. Application Data

(60) Provisional application No. 63/387,454, filed on Dec. 14, 2022.

(51) Int. Cl.

| | |
|---|---|
| ***C07K 16/32*** | (2006.01) |
| ***A61K 47/68*** | (2017.01) |
| ***A61K 51/10*** | (2006.01) |
| ***A61P 35/00*** | (2006.01) |
| ***C07K 14/705*** | (2006.01) |
| ***C07K 16/28*** | (2006.01) |
| ***C12N 5/0783*** | (2010.01) |

(52) U.S. Cl.

CPC .......... *C07K 16/32* (2013.01); *A61K 47/6851* (2017.08); *A61K 51/1045* (2013.01); *A61P 35/00* (2018.01); *C07K 14/7051* (2013.01); *C07K 14/70517* (2013.01); *C07K 14/70578* (2013.01); *C07K 16/2809* (2013.01); *C12N 5/0636* (2013.01); *C07K 2317/31* (2013.01); *C07K 2317/569* (2013.01); *C07K 2319/03* (2013.01); *C12N 2502/30* (2013.01)

(58) Field of Classification Search

CPC ................ C07K 16/32; C07K 14/7051; C07K 14/70517; C07K 14/70578; C07K 16/2809; C07K 2317/31; C07K 2317/569; C07K 2319/03; C07K 2317/22; C07K 2317/622; C07K 2317/92; C07K 16/30; A61K 47/6851; A61K 51/1045; A61K 40/11; A61K 40/31; A61K 40/4202; A61P 35/00; C12N 5/0636; C12N 2502/30

See application file for complete search history.

(56) References Cited

PUBLICATIONS

Kravchenko et al. Bulletin of RSMU. 2020. No. 5. p. 14-21 (Year: 2020).*

* cited by examiner

*Primary Examiner* — Sean E Aeder
*Assistant Examiner* — Yie Chia Lee
(74) *Attorney, Agent, or Firm* — Lee & Hayes, P.C.

(57) ABSTRACT

The present disclosure describes compositions and methods for treating solid tumors expressing mesothelin (MSLN) using chimeric antigen receptor (CAR) T cell therapy. The compositions comprise CARs with an extracellular domain that specifically binds MSLN. The extracellular domain comprises a single variable domain (VHH) antibody that targets MSLN. Polynucleotides encoding the anti-MSLN CAR constructs are provided. Pharmaceutical compositions comprising CAR T cells expressing the anti-MSLN CARs are also described. The CAR T cells demonstrate cytotoxicity against MSLN-expressing tumor cells in vitro and anti-tumor activity in vivo. Methods are provided for generating the CAR T cells by transfecting T cells with lentiviral or retroviral vectors carrying anti-MSLN CAR encoding sequences. The anti-MSLN CAR T cell therapy described herein provides an effective approach for treating solid tumors expressing MSLN, such as mesothelioma, ovarian cancer, pancreatic cancer, and lung cancer.

21 Claims, 12 Drawing Sheets

Specification includes a Sequence Listing.

NANOBODY TARGET MSLN AND USES IN CHIMERIC ANTIGEN RECEPTOR CELL THERAPY

CROSS REFERENCE TO RELATED APPLICATIONS

This application claims the benefit of U.S. Provisional Application 63/387,454, filed Dec. 14, 2022, which is incorporated by reference in its entirety.

SEQUENCE LISTING INFORMATION

The Sequence Listing associated with this application is provided in XML format in lieu of a paper copy and is hereby incorporated by reference into the specification. The name of the XML file containing the Sequence Listing is "SDS1.0126US.xml". The XML file is 24,447 bytes, was created on Nov. 27, 2023, and is being submitted electronically via PatentCenter.

TECHNICAL FIELD

The present disclosure relates to modified cells comprising chimeric antigen receptor (CAR) and uses thereof, and in particular, to compositions comprising the modified cells and methods of using the compositions for treating cancer.

BACKGROUND

Mesothelin (MSLN) is a cell surface protein overexpressed in several types of solid tumors, including mesothelioma, pancreatic, ovarian, and lung cancer. MSLN has been identified as a potential target for cancer therapy.

Nanobodies are antibody fragments derived from heavy chain only antibodies produced in camelids. They consist of a single monomeric variable domain (VHH) and have several advantages over conventional antibodies, including their small size, high stability, and ability to access cryptic epitopes. Recent studies have shown that chimeric antigen receptor (CAR) T cells expressing a nanobody targeting the B cell maturation antigen (BCMA) can induce remission in patients with relapsed/refractory multiple myeloma. This demonstrates the potential utility of nanobodies in CAR T cell therapy against solid tumors.

SUMMARY

The present disclosure describes nanobodies comprising VHH domains that specifically bind to MSLN. In embodiments, the VHH domains have amino acid sequences as set forth in SEQ ID NOs: 1-10. Polynucleotides encoding the anti-MSLN nanobodies and CAR constructs comprising the nanobodies are also described. The nanobodies and CARs can be used for treating solid tumors expressing MSLN, such as mesothelioma, ovarian cancer, pancreatic cancer, and lung cancer. Methods of preparing modified cells expressing the CARs are provided. Pharmaceutical compositions comprising the nanobody-based CAR T cells are described for use in cancer immunotherapy.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
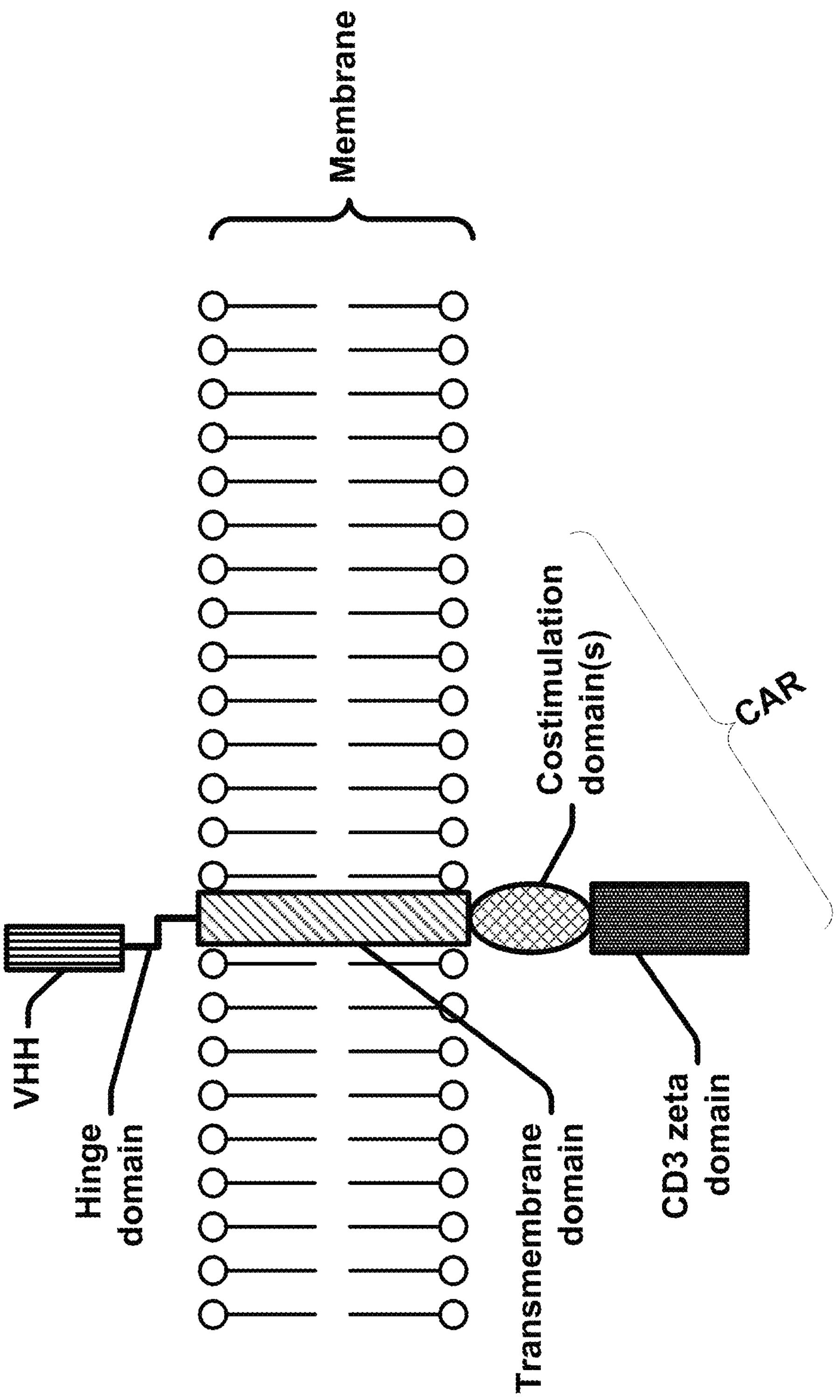
FIG. 1 illustrates a representative structure of a chimeric antigen receptor (CAR) commonly used in T cell engineering, showcasing various domains such as antigen-binding (VHH), hinge, transmembrane, costimulatory domain(s), and CD3 zeta domain.
Figure 2:
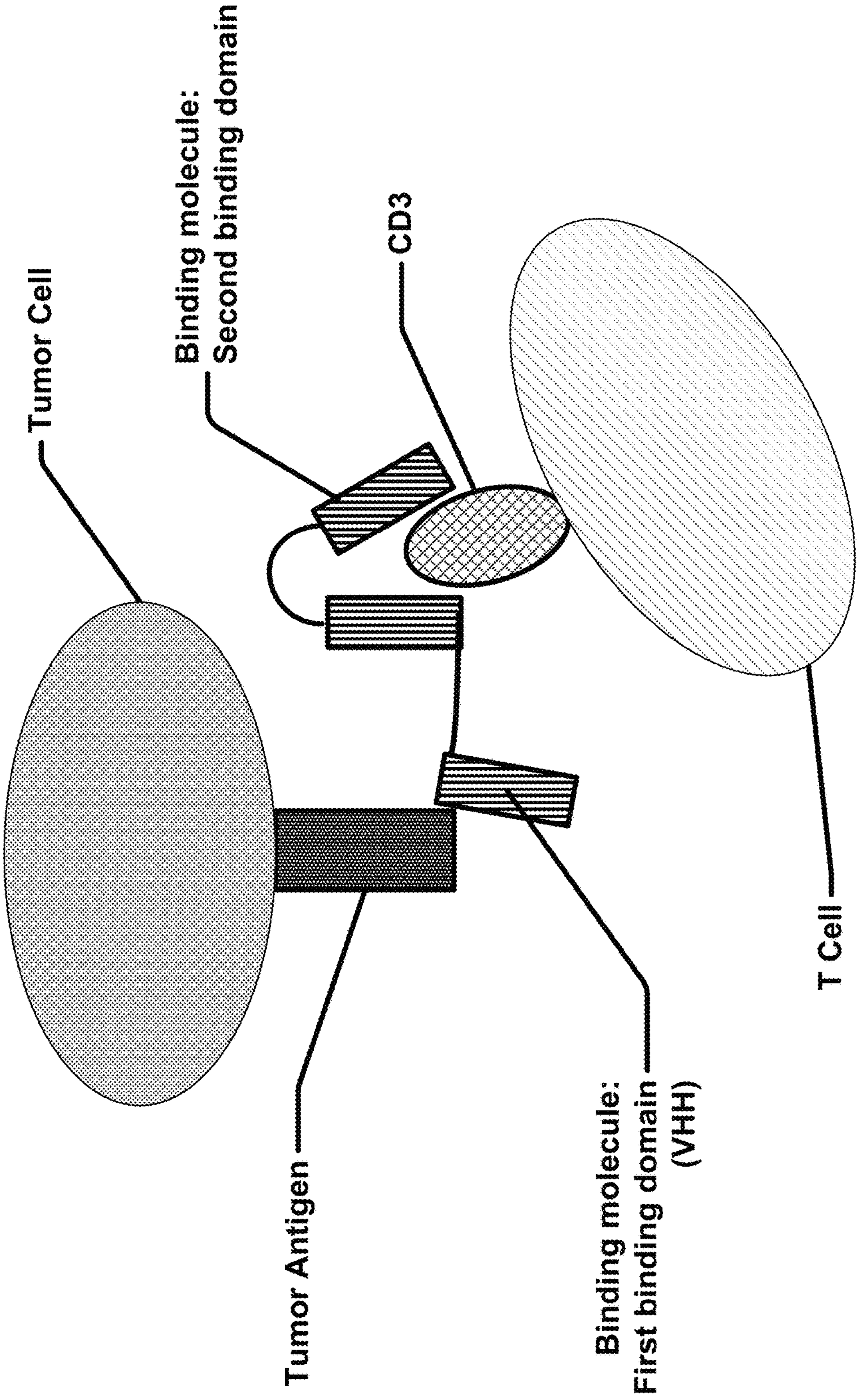
FIG. 2 depicts the interaction between a T cell and a tumor cell via a bispecific antibody.
Figure 3:
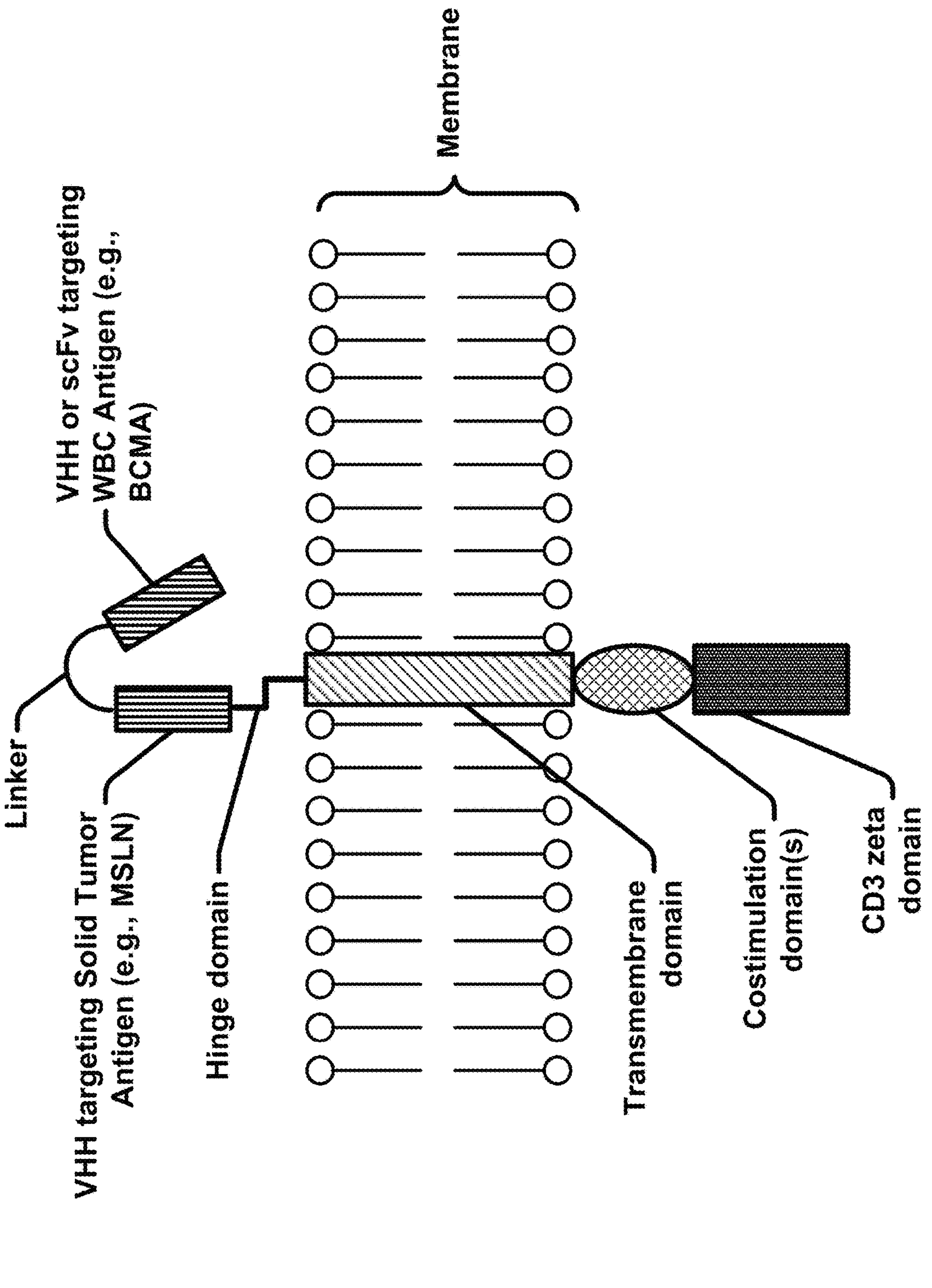
FIG. 3 shows a dual-specificity CAR structure designed to target two different antigens, with one binding domain specific for a solid tumor antigen (for example MSLN) and another targeting a white blood cell antigen (for example, BCMA), illustrating the modular nature of CAR for multi-target engagement.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. For example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms, including, for example, polyclonal antibodies, monoclonal antibodies, and Fv, Fab, Fab' and $F(ab)_2$ fragments, as well as single-chain antibodies and humanized antibodies (Harlow et al., 1999, In Using Antibodies: A Laboratory Manual, Cold Spring Harbor Laboratory Press, NY; Harlow et al., 1989, In Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment containing a complete antigen-recognition and -binding site. This fragment consists of a dimer of one heavy- and one light-chain variable region domain in a tight, non-covalent association. From the folding of these two domains emanates six hypervariable loops (3 loops each from the H and L chain) that contribute to the amino acid residues for antigen binding and confer antigen binding specificity to the antibody. However, even a single variable domain (or half of an Fv including only three complementarity determining regions (CDRs) specific for an antigen) can recognize and bind antigen, although at a lower affinity than the entire binding site (the dimer).

An "antibody heavy chain," as used herein, refers to the larger two types of polypeptide chains present in all antibody molecules in their naturally occurring conformations. An "antibody light chain," as used herein, refers to the smaller two types of polypeptide chains present in all antibody molecules in their naturally occurring conformations. K and A light chains refer to the two major antibody light chain isotypes.

The term "synthetic antibody" refers to an antibody generated using recombinant DNA technology, such as, for example, an antibody expressed by a bacteriophage. The term also includes an antibody generated by synthesizing a DNA molecule encoding the antibody and the expression of the DNA molecule to obtain the antibody or to obtain an amino acid encoding the antibody. Synthetic DNA is obtained using technology that is available and well known in the art.

In embodiments, an antibody is a single variable domain on a heavy chain (VHH) antibody, also referred to as Nanobodies®, which was discovered nearly 25 years ago. Heavy chain only antibodies (HcAb) are naturally produced by camelids and sharks. The antigen binding portion of the HcAb is comprised of the VHH fragment (See FIGS. 4 and 5).

The term "antigen" refers to a molecule that provokes an immune response, which may involve either antibody production, the activation of specific immunologically-competent cells, or both. Antigens include any macromolecule, including all proteins, peptides, or molecules derived from recombinant or genomic DNA. For example, DNA includes a nucleotide sequence or a partial nucleotide sequence encoding a protein or peptide that elicits an immune response and, therefore, encodes an "antigen," as the term is used herein. An antigen need not be encoded solely by a full-length nucleotide sequence of a gene. An antigen can be generated, synthesized, or derived from a biological sample, including a tissue sample, a tumor sample, a cell, or a biological fluid.

The term "anti-tumor effect," as used herein, refers to a biological effect associated with a decrease in tumor volume, a decrease in the number of tumor cells, a decrease in the number of metastases, a decrease in tumor cell proliferation, a decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies to prevent the occurrence of tumors in the first place.

The term "auto-antigen" or "self-antigen" refers to an antigen mistakenly recognized by the immune system as being foreign. Auto-antigens include cellular proteins, phosphoproteins, cellular surface proteins, cellular lipids, nucleic acids, and glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be related or unrelated to the recipient subject, but the donor subject has immune system markers that are similar to the recipient subject.

The term "xenogeneic" is used to describe a graft derived from a subject of a different species. For example, the donor subject is from a different species than the recipient subject, and the donor subject and the recipient subject can be genetically and immunologically incompatible.

The term "cancer" refers to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Cancers that may be treated include tumors that are not vascularized or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia, and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high-grade forms), multiple myeloma, Waldenstrom's macroglobulinemia, heavy chain disease, myelodysplastic syndrome, hairy cell leukemia, and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma, and brain metastases).

A solid tumor antigen is an antigen expressed on a solid tumor. In embodiments, solid tumor antigens are also expressed at low levels in healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL-13Rα2 (IL-13 receptor alpha 2) | Glioma |
| Mesothelin | Metastatic cancer |
| PSMA | Prostate cancer |

TABLE 1-continued

| Solid Tumor antigen | Disease tumor |
|---|---|
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |
| EGFR | Glioma-NSCL cancer |
| tMUC 1 | Cholangiocarcinoma, Pancreatic cancer, Breast |
| PSCA | pancreas, stomach, or prostate cancer |

Throughout this specification, unless the context requires otherwise, the words "comprise," "includes," and "including" will be understood to imply the inclusion of a stated step or element (ingredients or components) or group of steps or elements (ingredients or components) but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element or step listed after the phrase and can include other elements that do not interfere with or contribute to the activity or action specified in the disclosure for the listed elements or steps. Thus, the phrase "consisting essentially of" indicates that the listed elements are required or mandatory, but those other elements are optional and may or may not be present depending upon whether or not they affect the activity or action of the listed elements. In embodiments, those elements or steps that do not affect an embodiment are those elements or steps that do not alter the embodiment's ability in a statistically significant manner to perform a function in vitro or in vivo, such as killing cancer cells in vitro or in vivo.

The terms "complementary" and "complementarity" refer to polynucleotides (i.e., a sequence of nucleotides) related by the base-pairing rules. For example, the sequence "A-G-T" is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "costimulatory ligand" refers to a molecule on an antigen-presenting cell (e.g., an APC, dendritic cell, B cell, and the like) that specifically binds a cognate costimulatory molecule on a T cell, thereby providing a signal, in addition to the primary signal provided by, for instance, binding of a TCR/CD3 complex with an MHC molecule loaded with peptide, mediates a T cell response, including at least one of proliferation, activation, differentiation, and other cellular responses. A costimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand-receptor and a ligand that specifically binds B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, in combination with a primary signal, such as TCR/CD3 ligation, that leads to T cell proliferation and/or upregulation or downregulation of key molecules.

The terms "co-stimulatory signaling region," "co-stimulatory domain," and "co-stimulation domain" are used interchangeably to refer to one or more additional stimulatory domains in addition to a stimulatory or signaling domain such as CD3 zeta. The terms "stimulatory" or "signaling" domain (or region) are also used interchangeably when referring to, for example, CD3 zeta, the primary signaling domain. In embodiments, the co-stimulatory signaling domain and the stimulatory signaling domain can be on the same molecule or different molecules in the same cell.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis and wherein if the disease is not ameliorated, then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for the synthesis of other polymers and macromolecules in biological processes having either a defined sequence of nucleotides (i.e., rRNA, tRNA, and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter. The term "overexpression" refers to the production of a gene product in transgenic organisms or cells that exceeds levels of production in normal or non-transformed organisms or cells.

The term "expression vector" refers to a vector including a recombinant polynucleotide, including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses (AAV)) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared to ×100. For example, if 6 of 10 of the positions in two sequences are matched or homologous, then the two sequences are 60% homologous. For example, the DNA sequences ATTGCC and TATGGC share 50% homology. A comparison is made when two sequences are aligned to give maximum homology.

The term "immunoglobulin" or "Ig" refers to a class of proteins that function as antibodies. The five members included in this class of proteins are IgA, IgG, IgM, IgD, and IgE. IgA is the primary antibody that is present in body secretions, such as saliva, tears, breast milk, gastrointestinal secretions, and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule, such as a protein or nucleic acid. For example, an "isolated polynucleotide," as used herein, refers to a polynucleotide that has been purified from the sequences that flank it in a naturally-occurring state, e.g., a DNA fragment that has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may, in some versions, contain an intron(s).

The term "lentivirus" refers to a genus of the Retroviridae family. Lentiviruses are unique among retroviruses in being able to infect non-dividing cells; they can deliver a significant amount of genetic information into the DNA of the host cell, so they are one of the most efficient methods of a gene delivery vector. Moreover, the use of lentiviruses enables the integration of genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound and/or compared with the level of a response in an otherwise identical but untreated subject. The term encompasses perturbing and/or affecting a native signal or response, thereby mediating a beneficial therapeutic response in a subject, preferably a human.

Nucleic acid is "operably linked" when it is placed into a functional relationship with another nucleic acid sequence. For example, DNA for a sequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area, such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," "individual," and the like are used interchangeably herein and refer to any animal, such as a mammal, for example a human or any living organism amenable to the methods described herein. In embodiments, the patient, subject, or individual is a human or mammal. In embodiments, the term "subject" is intended to include living organisms in which an immune response can be elicited (e.g., mammals). Examples of subjects include humans and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for the prevention of a disease, condition, or disorder. Accordingly, the subject can also be in need of prevention of a disease condition or disorder. In embodiments, the disease is cancer.

The term "polynucleotide" or "nucleic acid" refers to mRNA, RNA, cRNA, rRNA, cDNA, or DNA. The term typically refers to a polymeric form of nucleotides of at least ten bases in length, either ribonucleotides or deoxynucleotides or a modified form of either type of nucleotide. The term includes all forms of nucleic acids, including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations, inclusive of mutations, additions, deletions, and substitutions, can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In embodiments, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions, and, in this regard, it is well understood in the art that some amino acids may be changed to others with broadly similar properties without changing the nature of the activity of the polypeptide. Polypeptide variants also encompass polypeptides in which one or more amino acids have been added, deleted, or replaced with different amino acid residues.

The term "promoter" refers to a DNA sequence recognized by the synthetic machinery of the cell or introduced synthetic machinery required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody that recognizes a specific antigen but does not substantially recognize or bind other molecules in a sample. For example, an antibody that specifically binds an antigen from one species may also bind that antigen from one or more species. However, such cross-species reactivity does not itself alter the classification of an antibody as specific. In another example, an antibody that specifically binds an antigen may also bind different allelic forms of the antigen. However, such cross reactivity does not itself alter the classification of an antibody as being specific. In embodiments, the terms "specific binding" or "specifically binding" can be used to describe to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A) in a reaction containing labeled "A," and the antibody will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein), and/or a protein molecule (a protein-binding protein). In the case of a protein-binding protein, it can bind to itself (to form homodimers, homotrimers, etc.), and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example, via engineering (altering one or more amino acids) of the recognition helix region of a naturally occurring zinc finger protein. Further, a Zinc finger binding domain may be fused with a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes).

"Cleavage" refers to the breakage of the covalent backbone of a DNA molecule. Cleavage can be initiated by a variety of methods, including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, sequence five ' GAATTC 3' is a target site for the Eco RI restriction endonuclease.

A "fusion" molecule is a molecule in which two or more subunit molecules are linked, preferably covalently. The subunit molecules can be the same chemical type of molecule or can be different chemical types of molecules. Examples of the first type of fusion molecule include but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include but are not limited to, a fusion between a triplex-forming nucleic acid and a polypeptide and a fusion between a minor groove binder and a nucleic acid.

Expression of a fusion protein in a cell can result from the delivery of the fusion protein to the cell or by delivery of a polynucleotide encoding the fusion protein to a cell, wherein the polynucleotide is transcribed, and the transcript is translated to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to gene activation and gene repression. Genome editing (e.g., cleavage, alteration, inactivation, random mutation) can be used to modulate expression. Gene inactivation refers to any reduction in gene expression as compared to a cell that does not include a ZFP, as described herein. Thus, gene inactivation may be partial or complete.

A "region of interest" is any region of cellular chromatin, such as, for example, a gene or a non-coding sequence within or adjacent to a gene in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences, or introns, or within non-transcribed regions, either upstream or downstream of the coding region. A region of interest can be as small as a single nucleotide pair or up to 2,000 nucleotide pairs in length or any integral value of nucleotide pairs.

By "statistically significant," it means that the result was unlikely to have occurred by chance. Statistical significance can be determined by any method known in art. Commonly used measures of statistical significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount and may include a decrease that is about 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by the binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-β and/or reorganization of cytoskeletal structures. CD3 zeta is not the only suitable primary signaling domain for a CAR construct with respect to the primary response. For example, back in 1993, both CD3 zeta and FcRγ were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T cell receptors" PNAS, 1993 Jan. 15; 90(2):720-4, showed that two CAR constructs in which an scFv was fused to "either the FcR gamma chain or the CD3 complex chain" triggered T cell activation and target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al. ("A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl. 1, May 2014, page S57) tested a CAR molecule in which an scFv was fused to "the transmembrane and the cytoplasmic domain of" a killer immunoglobulin-like receptor (KIR). Wang et al. reported that "a KIR-based CAR targeting mesothelin (SS 1-KIR) triggers antigen-specific cytotoxic activity and cytokine production that is comparable to CD3~-based CARs." A second publication from the same group, Wang et al. ("Generation of Potent T-cell Immunotherapy for Cancer Using DAP12-Based, Multichain, Chimeric Immunoreceptors" Cancer Immunol Res. 2015 July; 3(7):815-26), showed that a CAR molecule in which "a single-chain variable fragment for antigen recognition was fused to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that, when present on an antigen presenting cell (e.g., an APC, a dendritic cell, a B-cell, and the like), can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to the treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor, or another clinician. The term "therapeutically effective amount" includes the amount of a compound that, when administered, is sufficient to prevent the development of, or alleviate to some extent, one or more of the signs or symptoms of the disorder or disease being treated. The therapeutically effective amount will vary depending on the compound, the disease, its severity, and the age, weight, etc., of the subject to be treated.

The term "treat a disease" refers to the reduction of the frequency or severity of at least one sign or symptom of a disease or disorder experienced by a subject.

The term "transfected," "transformed," or "transduced" refers to a process by which an exogenous nucleic acid is transferred or introduced into the host cell. A "transfected," "transformed," or "transduced" cell is one that has been transfected, transformed, or transduced with an exogenous nucleic acid. The cell includes the primary subject cell and its progeny.

The term "vector" refers to a polynucleotide that comprises an isolated nucleic acid and that can be used to deliver the isolated nucleic acid to the interior of a cell. The cell can be an in vitro cell or an in vivo cell in a subject Numerous vectors are known in the art, including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds that facilitate the transfer of nucleic acid into cells, such as polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural functions. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiplying attenuating the HIV virulence genes; for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, a description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

T cells, or T lymphocytes, are a type of white blood cell of the immune system. There are various types of T cells, including T helper (TH) cells, cytotoxic T (TC) cells (T killer cells, killer T cells), natural killer T (NKT) cells, memory T (Tm) cells, regulatory T (Treg) cells, and gamma delta T (γδ T) cells.

T helper (TH) cells assist other lymphocytes, for example, activating cytotoxic T cells and macrophages and maturing B cells into plasma cells and memory B cells. These T helper cells express CD4 glycoprotein on their surface and are also known as CD4+ T cells. Once activated, these T cells divide rapidly and secrete cytokines.

Cytotoxic T (TC) cells destroy virus-infected cells and tumor cells and are also involved in transplant rejection. They express CD8 protein on their surface. Cytotoxic T cells release cytokines.

Natural Killer T (NKT) cells are different from natural killer cells. NKT cells recognize glycolipid antigens presented by CD1d. Once activated, NKT cells produce cytokine and release cell killing molecules.

Memory T (Tm) cells are long-lived and can expand to a large number of effector T cells upon re-exposure to their cognate antigen. Tm cells provide the immune system with memory against previously encountered pathogens. There are various subtypes of Tm cells, including central memory T (TCM) cells, effector memory T (TEM) cells, tissue resident memory T (TRM) cells, and virtual memory T cells. Tm cells are either CD4+ or CD8+ and usually CD45RO.

Regulatory T (Treg) cells shut down T cell mediated immunity at the end of an immune reaction and suppress autoreactive T cells that escaped the process of negative selection in the thymus. Subsets of Treg cells include thymic Treg and peripherally derived Treg. Both subsets of Treg require the expression of the transcription factor FOXP3.

Gamma delta T (γδ T) cells are a subset of T cells that possess a γδ T cell receptor (TCR) on the cell surface, as most T cells express the αβ TCR Chains. γδ T cells are less common in humans and mice and are mainly found in the gut mucosa, skin, lung, and uterus. They are involved in the initiation and propagation of immune responses.

Embodiments of the present disclosure relate to treating cancer using chimeric antigen receptor (CAR) cells. Embodiments relate to an isolated nucleic acid encoding a CAR, wherein the CAR comprises an extracellular domain, a transmembrane domain, and an intracellular domain, wherein the extracellular domain of the CAR binds an antigen of a solid tumor. For example, transcriptional data shows that the expression of antigens such as SLC6A3, KISS1R, and QRFPR in normal tissues is very low, but the expression of such antigens in cells related to renal cancer is high. Information on some of the antigens is provided below in Table 2.

TABLE 2

| Gene name | Subcellular localization | Organ mainly expressing | Target Tumor |
|---|---|---|---|
| SIGLEC15 | Plasma membrane | Expression in all normal tissues is very low | Urothelial cancer |
| SLC6A3 | Plasma membrane | Expression in all normal tissues is very low | Renal cancer |
| KISS1R | Plasma membrane | Expression in all normal tissues is very low | Renal cancer |
| QRFPR | Plasma membrane | Expression in all normal tissues is very low | Renal cancer: |
| GPR119 | Plasma membrane | Expression in all normal tissues is very low | Pancreatic cancer |
| CLDN6 | Plasma membrane | Expression in all normal tissues is very low | Endometrial cancer/ Urothelial cancer |
| UPK2 | Plasma membrane | Urethra/bladder | Urothelial cancer (including bladder cancer) |
| ADAM12 | Plasma membrane | placenta | Breast cancer, pancreatic cancer, and the like |
| SLC45A3 | Plasma membrane | prostate | Prostate cancer |
| ACPP | Plasma membrane | prostate | Prostate cancer |
| MUC21 | Plasma membrane | esophagus | Esophageal cancer |

TABLE 2-continued

| Gene name | Subcellular localization | Organ mainly expressing | Target Tumor |
|---|---|---|---|
| MUC16 | Plasma membrane | Cervical/Fallopian tube | Ovarian cancer |
| MS4A12 | Plasma membrane | the large intestine | Colorectal cancer |
| ALPP | Plasma membrane | Placenta/cervix | Endometrial cancer |
| SLC2A14 | Plasma membrane | testis | Testicular cancer |
| GS1-259H13.2 | Plasma membrane | testis | Thyroid cancer, glioma or testicular cancer, and other |
| ERVFRD-1 | Plasma membrane | Placenta or parathyroid | Kidney cancer, Urethral cancer, and many others |
| ADGRG2 | Plasma membrane | Epididymis | Ovarian cancer |
| ECEL1 | Plasma membrane | Ovary | Endometrial cancer |
| CHRNA2 | Plasma membrane | Prostate or cortex | Prostate cancer |
| GP2 | Plasma membrane | pancreas | Pancreatic cancer |
| PSG9 | Plasma membrane | placenta | Kidney cancer or liver cancer |

The T cell response in a subject refers to cell-mediated immunity associated with helper, killer, regulatory, and other types of T cells. For example, T cell response may include activities such as providing assistance to other white blood cells in immunologic processes and identifying and destroying virus-infected cells and tumor cells. T cell response in the subject may be measured via various indicators such as the number of virus-infected cells and/or tumor cells that T cells kill, the number of cytokines that T cells release, for example, in co-culturing with virus-infected cells and/or tumor cells, a level of proliferation of T cells in the subject, a phenotype change of T cells (e.g., changes to memory T cells), and level longevity or lifetime of T cells in the subject.

In embodiments, an in vitro killing assay may be performed by measuring the killing efficacy of CAR T cells by co-culturing CAR T cells with antigen-positive cells. CAR T cells may be considered to have a killing effect on the corresponding antigen-positive cells by showing a decrease in the number of corresponding antigen-positive cells co-cultured with CAR T cells and an increase in the release of IFNγ, TNFα, etc., as compared to control cells that do not express the corresponding antigen. Further, in vivo, the antitumor activity of the CAR T cells may be tested. For example, xenograft models may be established using the antigens described herein in immunodeficient mice. Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, –247-250 (2007)). To evaluate the anti-tumor activity of CAR T cells in vivo, immunodeficient mice bearing tumor xenografts were evaluated for CAR T cell anti-tumor activity (e.g., a decrease in mouse tumors and mouse blood IFNγ, TNFα, et al.).

The term "chimeric antigen receptor" or alternatively "CAR" refers to a recombinant polypeptide comprising at least an extracellular antigen binding domain, a transmembrane domain, and an intracellular domain (cytoplasmic domain) including an intracellular signaling domain. In embodiments, the domains in the CAR polypeptide are on the same polypeptide chain for example, comprising a chimeric fusion protein. In embodiments, the domains of the CAR polypeptide are not on the same molecule, for example, not contiguous with each other or are on different polypeptide chains.

In embodiments, the intracellular signaling domain includes a functional signaling domain derived from a stimulatory molecule and/or a co-stimulatory molecule, as described herein. In embodiments, the intracellular signaling domain includes a functional signaling domain derived from a primary signaling domain (e.g., a primary signaling domain of CD3-zeta). In embodiments, the intracellular signaling domain further includes one or more functional signaling domains derived from at least one co-stimulatory molecule. The co-stimulatory signaling region refers to a portion of the CAR, including the intracellular domain of a co-stimulatory molecule. Co-stimulatory molecules can include cell surface molecules for inducing an efficient response from the lymphocytes (in response to an antigen).

Between the extracellular domain and the transmembrane domain of the CAR, a spacer domain can be incorporated. As used herein, the term "spacer domain" generally means any oligo- or polypeptide that functions to link the transmembrane domain to the extracellular domain and/or the cytoplasmic domain in the polypeptide chain. A spacer domain may include up to 300 amino acids, 10 to 100 amino acids, or 25 to 50 amino acids.

In embodiments, the extracellular domain of a CAR includes an antigen binding domain (e.g., an scFv, a single domain antibody, or TCR, such as a TCR alpha binding domain or a TCR beta binding domain) that targets a specific tumor marker (e.g., a tumor antigen). Tumor antigens are proteins that are produced by tumor cells that elicit an immune response, particularly T cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, and mesothelin. For example, when the antigen that the CAR binds is CD19, the CAR thereof is referred to as CD19 CAR (19CAR, CD19CAR, CD19 CAR, or CD19-CAR), which is a CAR molecule that includes an antigen binding domain that binds CD19.

In embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID: 11), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides comprising about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect, or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, MSLN, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by a tumor. In embodiments, the binding element of the CAR includes any antigen binding moiety that, when bound to its cognate antigen, affects a tumor cell such that the tumor cell fails to grow, decrease in size, or dies.

In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In embodiments, the intracellular domain comprises a CD3 zeta signaling domain. Embodiments relate to a vector comprising the isolated nucleic acid sequence described herein. Embodiments relate to an isolated cell comprising the isolated nucleic acid sequence described herein.

Embodiments relate to a composition comprising a population of cells, including T cells comprising the CAR described herein. Embodiments relate to a CAR encoded by the isolated nucleic acid sequence described herein.

The cells, including CAR cells and modified cells, described herein can be derived from a stem cell. The stem cells may be adult stem cells, embryonic stem cells, non-human stem cells, cord blood stem cells, progenitor cells, bone marrow stem cells, induced pluripotent stem cells, totipotent stem cells, or hematopoietic stem cells. The cells can also be a dendritic cell, an NK-cell, a B-cell, or a T cell selected from the group consisting of inflammatory T lymphocytes, cytotoxic T lymphocytes, regulatory T lymphocytes, and helper T lymphocytes. In embodiments, the cells can be derived from the group consisting of CD4+T-lymphocytes and CD8+T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art can be used. In embodiments, the cells may be derived from a healthy donor, from a patient diagnosed with cancer, or from a patient diagnosed with an infection. In embodiments, the cells are part of a mixed population of cells that present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any type of cell that has the capacity for self-renewal and the ability to differentiate into other kinds of cells. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished on the basis of their origin and/or on the extent of their capacity for differentiation into other types of cells. Stem cells can include embryonic stem (ES) cells (i.e., pluripotent stem cells), somatic stem cells, induced pluripotent stem cells, and any other types of stem cells.

Pluripotent embryonic stem cells can be found in the inner cell mass of a blastocyst and have a high innate capacity for differentiation. For example, pluripotent embryonic stem cells have the potential to form any type of cell in the body. When grown in vitro for long periods of time, ES cells maintain pluripotency, and progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited number of different types of cells and have been described as multipotent. "Tissue-specific" stem cells normally give rise to only one type of cell. For example, embryonic stem cells can differentiate into blood stem cells (e.g., Hematopoietic stem cells (HSCs)), which can further differentiate into various blood cells (e.g., red blood cells, platelets, white blood cells, etc.).

Induced pluripotent stem cells (iPS cells or iPSCs) can include a type of pluripotent stem cell artificially derived from a non-pluripotent cell (e.g., an adult somatic cell) by inducing the expression of specific genes. Induced pluripotent stem cells are similar to naturally occurring pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be isolated from an adult stomach, liver, skin, and blood cells.

In embodiments, the CAR cells, the modified cell, or the cell is a T cell, an NK cell, a macrophage, or a dendritic cell. For example, the CAR cells, the modified cell, or the cell is a T cell.

In embodiments, the antigen binding molecule is a T Cell Receptor (TCR). In embodiments, the TCR is modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1. In embodiments, the TCR comprises TCRγ and TCRδ chains or TCRα and TCRβ chains. In embodiments, a T cell clone that expresses a TCR with a high affinity for the target antigen may be isolated. In embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle (e.g., a gammaretrovirus or lentivirus) may then be generated and tested for functionality (antigen specificity and functional avidity) and used to produce a clinical lot of the vector. An aliquot of the final product is then used to transduce the target T cell population (generally purified from patient PBMCs), which is expanded before infusion into the subject.

In embodiments, the APCs include dendritic cells, macrophages, Langerhans cells and B cells, or T cells.

In embodiments, the binding element of the CAR may include any antigen binding moiety that, when bound to its cognate antigen, affects a tumor cell; for example, it kills the tumor cell, inhibits the growth of the tumor cell, or promotes the death of the tumor cell.

The nucleic acid sequences coding for the desired molecules can be obtained using recombinant methods known in the art, such as, for example, by screening libraries from cells expressing the nucleic acid, deriving the nucleic acid from a vector known to include the same, or isolating directly from cells and tissues containing the same, using standard techniques. Alternatively, the nucleic acid of interest can be produced synthetically rather than cloned.

The embodiments of the present disclosure further relate to vectors in which the nucleic acid described herein is inserted. Vectors can be derived from retroviruses such as the lentiviruses that are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of low immunogenicity.

Viruses can be used to deliver nucleic acids into a cell in vitro and in vivo (in a subject). Examples of viruses useful for the delivery of nucleic acids into cells include retrovirus, adenovirus, herpes simplex virus, vaccinia virus, and adeno-associated virus.

There also exist non-viral methods for delivering nucleic acids into a cell, for example, electroporation, gene gun, sonoporation, magnetoreception, and the use of oligonucleotides, lipoplexes, dendrimers, and inorganic nanoparticles.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration into eukaryotes. Typical cloning vectors contain transcription and translation terminators, initiation sequences, and promoters useful for the regulation of the expression of the desired nucleic acid sequence.

Additional information related to the expression of synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the patient and the type and severity of the patient's disease, although appropriate dosages may be determined by clinical trials.

When "an immunologically effective amount," "an anti-tumor effective amount," "a tumor-inhibiting effective amount," "therapeutic amount," or "effective amount" is indicated, the precise amount of the compositions of the present disclosure to be administered can be determined by a physician with consideration of individual differences in age, weight, tumor size, the extent of infection or metastasis, and condition of the patient (subject). It can be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions can also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art by monitoring the patient for signs of disease and adjusting the treatment accordingly. In embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc.

Not to be bound by theory, using this multiple blood draw/multiple reinfusion protocol, certain populations of T cells can be selected.

The administration of the pharmaceutical compositions described herein can be carried out in any convenient manner, including by aerosol inhalation, injection, ingestion, transfusion, implantation, or transplantation. The pharmaceutical compositions described herein can be administered to a patient subcutaneously, intradermally, intratumorally, intranodal, intramedullary, intramuscularly, intravenously (i. v.), or intraperitoneally. In embodiments, the T cell compositions of the present disclosure are administered to a patient by intradermal or subcutaneous injection. In embodiments, the T cell compositions of the present disclosure are administered by i.v. Injection. The compositions of T cells may be injected directly into a tumor, lymph node, or site of infection. In embodiments of the present disclosure, cells activated and expanded using the methods described herein, or other methods known in the art where T cells are expanded to therapeutic levels, are administered to a patient in conjunction with (e.g., before, simultaneously, or following) any number of relevant treatment modalities, including but not limited to treatment with agents such as antiviral therapy, cidofovir, and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions of the present disclosure are administered to a patient in conjunction with (e.g., before, simultaneously, or following) bone marrow transplantation, T cell ablative therapy using either chemotherapy agents such as fludarabine, external-beam radiation therapy (XRT), cyclophosphamide, or antibodies such as OKT3 or CAMPATH. In embodiments, the cell compositions of the present disclosure are administered following B-cell ablative therapy, such as agents that react with CD20, e.g., Rituxan®. For example, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery.

The dosage of the above treatments to be administered to a patient will vary with the precise nature of the condition being treated and the recipient of the treatment. The scaling of dosages for human administration can be performed by a physician according to art-accepted practices depending on various factors.

Additional information on the methods of cancer treatment using engineered or modified T cells is provided in U.S. Pat. No. 8,906,682, incorporated by reference in its entirety.

In embodiments, the population of cells described herein is used in autologous CAR T cell therapy. In embodiment, CAR T cell therapy is allogeneic CAR T cell therapy, TCR T cell therapy, and NK cell therapy.

Embodiments relate to an in vitro method for preparing modified cells. The method may include obtaining a sample of cells from the subject. For example, the sample may include T cells or T cell progenitors. The method may further include transfecting the cells with a DNA encoding at least a CAR culturing the population of CAR cells ex vivo in a medium that selectively enhances the proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

Embodiments of the present disclosure relate to treating cancer using Chimeric Antigen Receptor (CAR) cells using a molecule associated with a gene fusion. Embodiments relate to an isolated nucleic acid sequence encoding a chimeric antigen receptor (CAR), wherein the CAR comprises an extracellular domain, a transmembrane domain, and an intracellular domain, wherein the extracellular domain binds a gene fusion antigen of a gene fusion.

As used herein, the term "gene fusion" refers to the fusion of at least a portion of a gene to at least a portion of an additional gene. The gene fusion need not include entire genes or exons of genes. In some instances, gene fusion is associated with alternations in cancer. A gene fusion product refers to a chimeric genomic DNA, a chimeric messenger RNA, a truncated protein, or a chimeric protein resulting from a gene fusion. The gene fusion product may be detected by various methods described in U.S. Pat. No. 9,938,582, which is incorporated as a reference herein. A "gene fusion antigen" refers to a truncated protein or a chimeric protein that results from a gene fusion. In embodiments, an epitope of a gene fusion antigen may include a part of the gene fusion antigen or an immunogenic part of another antigen caused by the gene fusion. In embodiments, the gene fusion antigen interacts with or is part of cell membranes.

In embodiments, the gene fusion comprises a fusion of at least a portion of a first gene to at least a portion of a second gene. In embodiments, the first gene and the second gene comprise a first gene and a second gene of a fusion listed in Table 3. In embodiments, the gene fusion antigen is associated with a condition listed in Table 3.

In embodiments, the detection of mRNA and protein expression levels of the target molecules (e.g., CARs and cytokines) in human cells may be performed using experimental methods such as qPCR and FACS. Further, target molecules specifically expressed in the corresponding tumor cells with very low expression or undetectable expression in normal tissue cells may be identified.

In embodiment, an in vitro killer assay, as well as a killing experiment of CAR T cells co-cultured with antigen-positive cells, can be performed. CAR T cells may exhibit a killing effect on the corresponding antigen-positive cells, a decrease in the number of corresponding antigen-positive cells co-cultured with CAR T cells, and an increase in the release of IFNγ, TNFα, etc., as compared to control cells that did not express the corresponding antigen.

In embodiments, an in vivo Killing Assay can be performed. For example, mice may be transplanted with corresponding antigen tumor cells, and tumorigenic transfusion of CAR T cells, and a decrease in mouse tumors and mouse blood IFNγ, TNFα, and other signals can be detected.

Embodiments relate to a method of eliciting and/or enhancing T cell response in a subject having a solid tumor or treating a solid tumor in the subject, the method comprising administering an effective amount of T cells comprising the CAR described herein. In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the intracellular domain comprises a CD3 zeta signaling domain.

Embodiments relate to a vector comprising the isolated nucleic acid described herein.

Embodiments relate to an isolated cell comprising the isolated nucleic acid sequence described herein. Embodiments relate to a composition comprising a population of T cells comprising the CAR described herein. Embodiments relate to a CAR encoded by the isolated nucleic acid sequence described herein. Embodiments relate to a method of eliciting and/or enhancing T-cell response in a subject or treating a tumor of the subject, the method comprising administering an effective amount of T cells comprising the CAR described herein.

Embodiments relate to methods or uses of the polynucleotides described herein. The methods or uses include providing a viral particle (e.g., AAV, lentivirus, or their variants) comprising a vector genome, the vector genome comprising the polynucleotide, wherein the polynucleotide is operably linked to an expression control element conferring transcription of the polynucleotide, and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information on the administration and preparation of the viral particle may be found in the U.S. Pat. No. 9,840,719 and Milani et al., Sci. Transl. Med. 11, eaav7325 (2019) 22 May 2019, which are incorporated herein by reference.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further, since an antibody has two heavy chains and two light chains, an antibody can have twelve CDRs altogether for binding antigens.

The present disclosure describes modified cells that include one or more different antigen binding domains. The modified cells can include at least two different antigen binding domains: a first antigen binding domain for expanding and/or maintaining the genetically modified cells and a second antigen binding domain for killing a target cell, such as a tumor cell. For example, the first antigen binding domain binds a surface marker, such as a cell surface molecule of a white blood cell (WBC) (e.g., CD19), and the second antigen binding domain binds a target antigen on tumor cells. In embodiments, the cell surface molecule is a surface antigen of a WBC. In embodiments, the target antigen on tumor cells comprises one or more of SIGLEC15, SLC6A3, KISS1R, QRFPR, GPR119, CLDN6, UPK2, ADAM12, SLC45A3, ACPP, MUC21, MUC16, MS4A12, or ALPP. The at least two antigen binding domains may be located on the same or different modified cells. For example, the modified cells may include a modified cell including a CAR binding CD19, a modified cell including a CAR binding to ACPP, a modified cell including a CAR binding CD19 and ACPP, and/or a modified cell including two CARs that respectively bind CD19 and ACPP. In embodiments, the modified cells may be used to treat a subject having cancer.

In embodiments, the modified cells described herein include a CAR molecule comprising at least two different antigen binding domains. The CAR molecule can be a bispecific CAR molecule. For example, the two antigen binding domains can be on the same CAR molecule, on different CAR molecules, or on a CAR molecule and T cell receptor (TCR). A single CAR can include at least two different antigen binding domains, or the two different antigen binding domains are each on a separate CAR molecule. The at least two different antigen binding domains can be on the same CAR molecule or different CAR molecules but in the same modified cell. Moreover, the at least two different antigen binding domains can be on a CAR molecule and a T cell receptor in the same modified cell. In embodiments, the bispecific CAR molecule may include a binding domain binding an antigen of WBC (e.g., CD19) and a binding domain binding a solid tumor antigen. In embodiments, the bispecific CAR molecule may include two binding domains binding two different solid tumor antigens.

In embodiments, the at least two different antigen binding domains are on different CAR molecules, which are expressed by different modified cells. Further, the one or more different antigen binding domains are on a CAR molecule and a T cell receptor, which are expressed by different modified cells.

Related sequences are provided in this Application and in Applications Nos: PCT/CN2016/075061, PCT/CN2018/08891, PCT/US21/28429, and PCT/US19/13068, which are incorporated by reference in their entirety.

In embodiments, the compositions and/or methods described herein can be combined with techniques associated with CoupledCAR® described in PCT Publication Nos: WO2020106843 and WO2020146743, which are incorporated in their entirety.

In embodiments, the antibody is a nanobody (single domain antibody, sdAb) comprising or consisting essentially of a VHH (single variable domain on a heavy chain) domain. In embodiments, the antibody is conjugated to a cytotoxic agent, and the cytotoxic agent is a radioactive isotope or a toxin. In embodiments, the antibody is a bispecific antibody comprising a VHH domain and an antibody or antibody fragment, for example, scFv, targeting CD3, and a linker.

In embodiments, the antibody comprises or consists essentially of a VHH domain and one or more constant domains, such as CH2 and CH3. In embodiments, the antibody is structurally similar to an alpaca antibody comprising or consisting essentially of a VHH domain, a CH2 domain, and a CH3 domain. In embodiments, the antibodies described herein comprising the VHH domain do not include the VL (variable light) and CL (constant light) domains.

The present disclosure describes a CAR comprising an antigen binding domain comprising the antibody that binds MSLN, as described herein. Embodiments describe a polynucleotide that encodes the antibody or the CAR. Embodiments describe a modified cell comprising the polynucleotide. In embodiments, the modified cell is a T cell or NK cell.

The present disclosure describes a population of modified immune cells comprising the CAR. In embodiments, the composition comprises a first population of cells comprising a first CAR binding a first antigen and a second population of cells comprising a second CAR binding a second antigen, wherein the second antigen is a tumor antigen and is different from the first antigen, and the first population and/or the second population of cells comprise one or more polynucleotides described herein.

The present disclosure describes the use of the composition comprising a first population and a second population of cells or a method of using the composition to enhance the expansion of cells in a subject in need thereof or treating a subject having cancer, the method comprising administering an effective amount of the composition to the subject, the subject having a form of cancer expressing a tumor antigen. In embodiments, the expansion of the second population of cells in the subject is greater than the expansion of the second population of cells in a subject that is administered with the second population of cells but not the first population of cells. In embodiments, the expansion is measured based on the number of the second population of cells or copy numbers of DNA encoding the second CAR. In embodiments, the cells are T cells, NK cells, macrophages, or dendritic cells. In embodiments, the first antigen comprises a cell surface molecule of a white blood cell (WBC), a tumor antigen, or a solid tumor antigen. In embodiments, the WBC is a granulocyte, a monocyte, or a lymphocyte. In embodiments, the WBC is a B cell. In embodiments, the cell surface molecule of the WBC is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the WBC is CD19, CD20, CD22, or BCMA. In embodiments, the cell surface molecule of the WBC is CD19 or BCMA. In embodiments, the tumor antigen is a solid tumor antigen.

In embodiments, the modified cells comprise a nucleic acid sequence encoding a binding molecule and a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD160. In embodiments, the inhibitory immune checkpoint molecule is modified PD-1. In embodiments, the modified PD-1 lacks a functional PD-1 intracellular domain for PD-1 signal transduction; interferes with a pathway between PD-1 of a human T cell of the human cells and PD-L1 of a certain cell; comprises or is a PD-1 extracellular domain or a PD-1 transmembrane domain, or a combination thereof; comprises a modified PD-1 intracellular domain comprising a substitution or deletion as compared to a wild-type PD-1 intracellular domain; or comprises or is a soluble receptor comprising a PD-1 extracellular domain that binds PD-L1 of a certain cell.

In embodiments, the modified cell has a reduced expression of the endogenous T cell receptor alpha constant (TRAC) gene. In embodiments, the modified cells include a nucleic acid sequence encoding human telomerase reverse transcriptase (hTERT), a nucleic acid encoding simian virus large T antigen (SV40LT), or a combination thereof. In embodiments, the modified cells include a nucleic acid sequence encoding hTERT and a nucleic acid encoding SV40LT. In embodiments, the expression of hTERT is regulated by an inducible expression system. In embodiments, the expression of SV40LT gene is regulated by an inducible expression system. In embodiments, the inducible expression system is rTTA-TRE, which increases or activates the expression of SV40LT gene, hTERT gene, or a combination thereof. In embodiments, the modified cells include a nucleic acid sequence encoding a suicide gene. In embodiments, the suicide gene includes an HSV-TK suicide gene system, and/or the modified cell can be induced to undergo apoptosis.

In embodiments, the modified cells include a nucleic acid sequence encoding a cytokine. In embodiments, the modified cells include a nucleic acid sequence encoding IL-6, IFNγ, IL-12, and/or IL-2.

The present disclosure describes an antibody that binds MSLN, wherein the antibody comprises a VHH domain comprising one of SEQ ID NOs: 1-10. Embodiments describe a polynucleotide that encodes the antibody. Embodiments describe a modified cell comprising the polynucleotide. Embodiments describe a CAR comprising an extracellular domain comprising the antibody described herein. In embodiments, the modified cell is a T cell or NK cell. In embodiments, the antibody comprises SEQ ID NO: 8 or 9. In embodiments, the antibody is a nanobody. In embodiments, the antibody is conjugated to a cytotoxic agent, and the cytotoxic agent is a radioactive isotope or a toxin. In embodiments, the antibody is a bispecific antibody comprising the VHH domain described herein, a linker, and an antibody targeting CD3. The antibody targeting CD3 can be a scFv antibody.

The present disclosure describes a composition comprising a population of the modified cells comprising a CAR comprising the antibody described herein. In embodiments, the modified cells comprise a polynucleotide encoding a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD160. In embodiments, the modified cells have reduced expression of the endogenous T cell receptor alpha constant (TRAC) gene. In embodiments, the modified cells comprise a polynucleotide encoding hTERT, a nucleic acid encoding SV40LT, or a combination thereof. In embodiments, the modified cells comprise a polynucleotide encoding a cytokine. In embodiments, the modified cells include a polynucleotide encoding at least one of IL-6, IFNγ, IL-12, and IL-2.

The present disclosure relates to an antibody fragment for targeting cancer cells. This antibody fragment comprises a VHH, which includes one of the amino acid sequences denoted as SEQ ID NOs: 1-10. Notably, this VHH has specificity for binding to mesothelin (MSLN), a protein commonly overexpressed in certain types of cancer.

In embodiments, the antibody fragment includes a VHH that features the amino acid sequence of either SEQ ID NO: 9 or SEQ ID NO: 8, potentially demonstrating enhanced binding affinity or specificity to MSLN. In embodiments, the antibody fragment is designed with a VHH fused to a human IgG constant region. In embodiments, the human IgG constant region fused to the VHH is selected from subclass IgG1 or IgG3, potentially conferring increased stability or half-life. In embodiments, the VHH is conjugated to a cytotoxic agent, which may be either a radioactive isotope or a toxin, thereby enhancing the fragment's therapeutic efficacy through targeted cell death. In embodiments, the VHH domain comprises the amino acid sequence of SEQ ID NO: 1, which can demonstrate particular efficacy in neutralizing MSLN activity. In embodiments, the VHH domain is glycosylated at specific sites to enhance its stability and extend its half-life in the bloodstream. In embodiments, the cytotoxic agent conjugated to the VHH domain is a chemotherapeutic drug, such as Doxorubicin, specifically formulated for slow release.

In embodiments, a chimeric antigen receptor (CAR) is created with an extracellular domain, a transmembrane domain, and an intracellular domain. The extracellular domain comprises the VHH, enabling CAR T cells to target MSLN-expressing cells specifically. In embodiments, the CAR includes an amino acid sequence from either SEQ ID NO: 9 or SEQ ID NO: 8. In embodiments, there exists a polynucleotide that encodes either the VHH or the CAR. In embodiments, the extracellular domain of the CAR further comprises an additional signaling domain, such as 4-1BB or CD28, to provide co-stimulatory signals to the T cells.

In embodiments, a modified cell containing the polynucleotide described herein is prepared. In embodiments, the modified cell comprising the polynucleotide is a T cell or a natural killer (NK) cell.

In embodiments, a polyspecific binding molecule (PBM) is prepared with at least a first binding domain that binds a T cell and a second binding domain. The second binding domain includes an amino acid sequence from either SEQ ID NO: 9 or SEQ ID NO: 8. In embodiments, the first binding domain in the PBM includes a scFv that binds to CD3, thereby recruiting T cells to the targeted MSLN-expressing cells. In embodiments, the PBM is a bispecific antibody. In embodiments, the polyspecific binding molecule (PBM) further includes a third binding domain that binds a checkpoint inhibitor, such as PD-1 or CTLA-4.

In embodiments, a pharmaceutical composition is formulated containing the VHH, along with a pharmaceutically acceptable carrier, such as a saline solution, lipid formulation, or other biocompatible carriers. In embodiments, the pharmaceutical composition includes additional therapeutic agents like chemotherapeutic agents, immunomodulatory agents, or anti-inflammatory agents. In embodiments, the pharmaceutical composition is suited for intravenous, subcutaneous, or intramuscular administration. In embodiments, the pharmaceutical composition is presented in a lyophilized form suitable for reconstitution. In embodiments, a pharmaceutical composition is formulated containing the modified cell, along with a pharmaceutically acceptable carrier that facilitates the cell's viability and delivery to the target site. In embodiments, the pharmaceutical composition further includes an immunostimulatory cytokine, such as IL-2 or IL-12, to promote immune activation. In embodiments, the pharmaceutical composition is prepared for intravenous administration. In embodiments, the pharmaceutical composition is cryopreserved for later use. In embodiments, a pharmaceutical composition is formulated containing the polynucleotide and a pharmaceutically acceptable carrier. In embodiments, the pharmaceutical composition includes a liposomal delivery system for enhanced efficacy, allowing for better cellular uptake and distribution. In embodiments, the pharmaceutical composition is suitable for intramuscular or intradermal administration. In embodiments, a pharmaceutical composition includes the polyspecific binding molecule (PBM), along with a pharmaceutically acceptable carrier. In embodiments, the pharmaceutical composition includes additional therapeutic agents, such as chemotherapeutic agents, immunomodulatory agents, or anti-inflammatory agents. In embodiments, the pharmaceutical composition is appropriate for intravenous, subcutaneous, or intramuscular administration. In embodiments, the pharmaceutical composition is encapsulated in nanoparticles for targeted delivery to tumor sites. In embodiments, the pharmaceutical composition is formulated with pH-sensitive materials to ensure release only in the acidic tumor environment. In embodiments, the pharmaceutical composition is suitable for intrathecal administration for treating brain tumors.

In embodiments, the present disclosure describes a method for treating a subject with a tumor expressing MSLN. This method involves administering any of the pharmaceutical compositions described herein to the subject. In embodiments, a method for treating subjects with non-small cell lung cancer expressing MSLN is formulated, which involves administering the pharmaceutical composition as described herein.

The present disclosure relates to an antibody fragment that includes a VHH domain engineered for enhanced affinity towards MSLN, as evidenced by an equilibrium dissociation constant (Kd) of less than 10 nM.

In embodiments, the cytotoxic agent conjugated to the VHH domain is a chemotherapeutic drug, such as Doxorubicin, designed for pH-sensitive release, thereby achieving cytotoxicity in the acidic tumor microenvironment.

In embodiments, the intracellular domain of the CAR further comprises an additional signaling domain, such as 4-1BB or CD28, to provide co-stimulatory signals essential for T-cell activation and persistence.

In embodiments, the pharmaceutical compositions described herein are formulated with excipients that enhance the solubility and stability of the active ingredients, resulting in a shelf-life of at least two years when stored at 2-8° C. In embodiments, the pharmaceutical compositions are encapsulated in nanoparticles coated with tumor-targeting ligands, enhancing targeted delivery to tumor sites. In embodiments, the pharmaceutical compositions are suitable for intrathecal administration and is formulated to cross the blood-brain barrier effectively.

The present disclosure relates to an isolated nucleic acid encoding a chimeric antigen receptor (CAR) designed with an extracellular domain, a transmembrane domain, and an intracellular domain. The extracellular domain is engineered to bind to MSLN and comprises of one of the amino acid sequences of SEQ ID NO: 1-10.

In embodiments, the amino acid sequence of the CAR is SEQ ID NO: 9 or SEQ ID NO: 8. In embodiments, the CAR's intracellular domain includes a CD3 zeta signaling domain and one or more co-stimulatory signaling regions. These co-stimulatory regions comprise, consist essentially of, or consist of an intracellular domain of a co-stimulatory molecule, which can be selected from a group including CD27, CD28, 4-1BB, OX40, CD30, CD40, PD-1, ICOS, LFA-1, CD2, CD7, LIGHT, NKG2C, and B7-H3. In embodiments, the isolated nucleic acid is housed within a vector, providing a vehicle for delivery into target cells.

In embodiments, cells are engineered to include the isolated nucleic acid, enabling them to express the CAR for targeted therapies. In embodiments, the engineered cells can also include one or more of the following features: a nucleic acid encoding a dominant negative form of an inhibitory immune checkpoint molecule, reduced expression of an endogenous TRAC gene, a nucleic acid encoding hTERT or SV40LT, a nucleic acid encoding a suicide gene, a nucleic acid encoding cytokines such as IL-6, IFNγ, IL-12, and/or IL-2. In embodiments, a composition includes a population of cells containing the isolated nucleic acid or the engineered cells. In embodiments, the cell population in the composition consists of lymphocytes, including but not limited to T cells, NK cells, macrophages, or dendritic cells. In embodiments, when the lymphocytes are T cells, a subset of these T cells includes a CAR that binds to a cell surface molecule of a white blood cell (WBC). In embodiments, the WBCs are B cells, and the cell surface molecule is one of CD19, CD22, CD20, BCMA, or others. In embodiments, the compositions are prepared as pharmaceutical formulations suitable for therapeutic use.

In embodiments, a method is described to stimulate a T cell response in a population of MSLN-expressing cells using the pharmaceutical composition. In embodiments, a method for stimulating an immune response is disclosed, targeting a population of MSLN-expressing cells using the pharmaceutical composition.

The present disclosure relates to a method for stimulating a T cell response against a tumor expressing MSLN. This method involves isolation of T cells are from a subject's peripheral blood using Ficoll density gradient centrifugation; transducing the isolated T cells are with a lentiviral vector comprising an isolated nucleic acid that encodes a chimeric antigen receptor (CAR) specific for MSLN; expanding the transduced T cells in vitro using a culture medium enriched with interleukin-2 (IL-2); and formulating the expanded, transduced T cells into a pharmaceutical composition that is suitable for intravenous injection; administering: the pharmaceutical composition o the subject through intravenous injection; and after administration monitoring the subject for T cell activation markers, including but not limited to increased levels of circulating cytokines, such as IL-6, IL-12, and IFNγ. The composition can include excipients such as saline, DMSO, or other biocompatible solvents.

In embodiments, a method for stimulating an immune response against a population of cells that express MSLN involves identifying a target population of cells that express MSLN using immunohistochemistry; and preparing a pharmaceutical composition comprising a population of modified T cells that contain an isolated nucleic acid encoding a chimeric antigen receptor (CAR) specific for MSLN. The pharmaceutical composition can also include specific excipients for stability, delivery, and administration. The pharmaceutical composition is delivered to the target site, such as a tumor mass, using localized injection techniques like fine-needle aspiration.

The present disclosure relates to a pharmaceutical composition encompassing a population of modified CAR T cells along with a pharmaceutically acceptable carrier. Notably, these CAR T cells possess the ability to bind to MSLN. The CAR is a VHH domain that comprises one of the amino acid sequences of SEQ ID NO: 1-10. This pharmaceutical composition serves as the cornerstone of therapeutic applications aiming to target cells expressing MSLN, potentially providing a more focused approach to immunotherapy.

In embodiments, the VHH domain integral to the CAR comprises the amino acid sequence specified as either SEQ ID NO: 9 or SEQ ID NO: 8. This embodiment adds an additional layer of specificity, potentially enhancing the affinity or specificity of CAR T cells toward mesothelin-expressing cells.

In embodiments, the population of modified CAR T cells also incorporates a polynucleotide encoding a first antigen binding molecule that binds a first antigen. This first antigen binding molecule has an affinity for a cell surface molecule present in B cells. The modified cells in this composition can be T cells, natural killer (NK) cells, or dendritic cells, thereby offering a multifaceted immune response.

In embodiments, the pharmaceutical composition comprises a mixed population of modified cells. This heterogeneous population includes cells modified with the first antigen binding molecule and cells modified with the CAR. Such a mixed population could potentially provide a more comprehensive and synergistic therapeutic approach.

In embodiments, the first antigen binding molecules are either CARs or antibodies that bind the cell surface molecule. This broadens the type of antigen-binding molecules involved, thereby increasing the modality of the therapeutic application.

In embodiments, the CARs are characterized by an extracellular domain, a transmembrane domain, and an intracellular domain. This establishes the structural elements of the CAR, which are potentially important for its functional performance.

In embodiments, the intracellular domain of the CAR includes a co-stimulatory domain featuring an intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, or a combination thereof. This embodiment could regulate the signaling pathways and, by extension, the activity of the CAR T cells.

In embodiments, the first antigen bound by the first antigen-binding molecule may be CD19, CD22, CD20, BCMA, CD5, CD7, CD2, CD16, CD56, CD30, CD14, CD68, CD11b, CD18, CD169, CD1c, CD33, CD38, CD138, or CD13. This increases the types of cells that can be targeted, thereby widening the therapeutic scope.

In embodiments, the modified cells are specifically T cells, which are known for their potent role in cell-mediated immunity and are often the focus of CAR T cell therapies.

In embodiments, the method for preparing the pharmaceutical composition involves contacting cells with a first vector and a second vector, each containing a polynucleotide encoding the respective antigen binding molecules. These vectors introduce the molecules into T cells, NK cells, or dendritic cells to obtain a mixed population of modified cells. This offers a streamlined approach to generating the pharmaceutical composition.

The present disclosure describes a pharmaceutical composition that includes CAR T cells engineered to specifically bind to MSLN. In addition to these CAR T cells and a pharmaceutically acceptable carrier, the composition further includes a chemotherapeutic agent selected from the group consisting of doxorubicin, cisplatin, and paclitaxel. This combination aims to provide synergistic effects, enhancing the therapeutic efficacy against esothelin-expressing cells, while also leveraging the cytotoxic mechanisms of the included chemotherapeutic agents.

In embodiments, the pharmaceutical composition contains CAR T cells designed to bind MSLN and an immunomodulatory agent selected from the group consisting of lenalidomide, pomalidomide, and thalidomide. This embodiment has the potential to modulate the immune system further and may provide additive or synergistic benefits when combined with the CAR T cell treatment.

The present disclosure relates to a method for synthesizing a variable domain of heavy chain antibody (VHH) that specifically binds to MSLN. This method includes isolating mRNA from a B cell, reverse transcribing the mRNA into cDNA, and amplifying the cDNA to produce the VHH domain comprising one of the amino acid sequences of SEQ ID NO: 1-10.

The present disclosure relates to a method for formulating a pharmaceutical composition that comprises CAR T cells targeting MSLN. The method involves mixing these CAR T cells with a pharmaceutically acceptable carrier and adjusting the pH to fall within the range of 6.0 to 7.5. Such pH optimization can be crucial for maintaining the stability and functionality of the CAR T cells. In embodiments, CAR comprising SEQ ID NO: 11 is designed to target MSLN. Similarly, the CARs comprising SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20 are each designed to target MSLN. These CAR constructs, each with a distinct amino acid sequence, target the MSLN antigen, potentially offering a range of therapeutic options for addressing MSLN-expressing tumors.

The present disclosure relates to a method for administering a pharmaceutical composition comprising CAR T cells designed to specifically bind MSLN. This method includes preparing an intravenous infusion and administering this infusion to the subject in need thereof at a dosage ranging from $1\times10^6$ to $1\times10^8$ cells per kilogram of body weight, providing a standardized yet flexible dosing regimen for different patient needs.

The present disclosure relates to a method for evaluating the efficacy of CAR T cells targeted to MSLN. This involves exposing the CAR T cells to mesothelin-expressing tumor cells and measuring the subsequent release of cytokines as an indicator of CAR T cell activation, providing an in vitro or in vivo indication of therapeutic efficacy.

The present disclosure relates to a method for ensuring the quality of a pharmaceutical composition containing CAR T cells that bind specifically to MSLN. This quality control method involves performing a purity test to confirm the absence of contaminants and conducting a stability test to ensure the viability of the CAR T cells over a designated time frame, thereby guaranteeing a product that meets specified quality benchmarks.

The present disclosure relates to a pharmaceutical composition for treating cancers that express MSLN. The active component of the composition includes CAR T cells that specifically bind MSLN. These CAR T cells comprise a variable domain of heavy chain antibody (VHH) comprising one of the amino acid sequences of SEQ ID NO: 1-10. The CAR T cells are present in an amount ranging from $1\times10^6$ to $1\times10^8$ cells per milliliter. The inactive component includes a pharmaceutically acceptable carrier made of saline solution and a stabilizing agent, such as human serum albumin or polyethylene glycol. The carrier is present in an amount sufficient to bring the total volume to 100 milliliters. The CAR T cells are suspended in this carrier. The composition is designed to have a stability of at least 12 months when stored at −80° C. and to have a controlled release rate of the CAR T cells upon administration. The composition is in a liquid form suitable for intravenous administration.

The present disclosure relates to a method of treating a subject diagnosed with cancers that express MSLN. The method involves administering CAR T cells that specifically bind MSLN. These CAR T cells comprise a VHH comprising one of the amino acid sequences of SEQ ID NO: 1-10. The treatment is designed for MSLN-expressing cancers, including mesothelioma and ovarian cancer. The CAR T cells are administered intravenously at a dosage of $1\times10^6$ to $1\times10^8$ cells per kilogram of body weight. Optionally, the treatment can be combined with a chemotherapeutic agent like doxorubicin, cisplatin, or paclitaxel. The method is particularly effective for subjects who have failed at least one prior line of therapy for MSLN-expressing cancer. The efficacy of the treatment is measured by a reduction in tumor size of at least 30%, as assessed by radiographic imaging within 12 weeks of the initial administration.

The present disclosure relates to a method for preparing a pharmaceutical composition that includes CAR T cells specifically binding to MSLN. The starting materials include isolated T cells from a subject and a vector containing a nucleic acid sequence encoding a VHH comprising one of the amino acid sequences of SEQ ID NO: 1-10. Lentiviral vectors are used for transfection at a multiplicity of infection (MOI) of 3. The culture medium includes RPMI 1640, 10% fetal bovine serum, and 1% penicillin-streptomycin, and the culturing conditions are 37° C. and 5% $CO_2$. The method involves isolating T cells, transfecting them with the lentiviral vector, culturing the transfected T cells, and then harvesting and purifying the CAR T cells using fluorescence-activated cell sorting (FACS). The method aims to achieve a CAR T cell purity level of at least 95% and a yield of at least $1\times10^8$ cells. The method excludes the use of retroviral vectors and culture conditions below 37° C. or above 40° ° C.

The present disclosure relates to a hybrid method for treating a subject diagnosed with or having a tumor that expressing MSLN. The method involves administering a pharmaceutical composition that includes CAR T cells. These CAR T cells comprise a VHH comprising one of the amino acid sequences of SEQ ID NO: 1-10. The composition is prepared by a method that includes isolating T cells, transfecting them with a lentiviral vector, culturing the transfected T cells, and then harvesting and purifying the CAR T cells to achieve a purity level of at least 95%. The method results in a reduction of tumor size by at least 30%.

The present disclosure relates to a method for synthesizing a nucleic acid sequence encoding a VHH that specifically binds MSLN. The VHH comprises one of the amino acid sequences of SEQ ID NO: 1-10. The method involves utilizing CRISPR/Cas9 gene editing technology to insert the nucleic acid sequence into a specified locus of a host cell genome, culturing the host cell under conditions that induce expression of the VHH, and isolating and purifying the expressed VHH to achieve a purity level of at least 98%.

The present disclosure relates to a method for treating a subject diagnosed with pleural mesothelioma. The treatment involves administering a pharmaceutical composition that includes CAR T cells. These CAR T cells comprise a VHH with one of the amino acid sequences defined in SEQ ID NO: 1-10.

The present disclosure relates to a formulation comprising CAR T cells and a pharmaceutically acceptable carrier. The CAR T cells comprise a VHH comprising one of the amino acid sequences of SEQ ID NO: 1-10. The composition is formulated as a slow-release injectable gel.

The present disclosure relates to a method of administration for treating a subject having a tumor expressing MSLN. The treatment involves administering a pharmaceutical composition that includes CAR T cells via intravenous infusion. These CAR T cells comprise a VHH with one of the amino acid sequences of SEQ ID NO: 1-10.

The present disclosure relates to the use of an isolated nucleic acid in the manufacture of a medicament for treating mesothelin-expressing cancers. Notably, the isolated nucleic acid encodes a chimeric antigen receptor (CAR) that contains an extracellular domain capable of binding MSLN.

Furthermore, this domain includes one of the amino acid sequences of SEQ ID NO: 1-10.

In embodiments, the use of the isolated nucleic acid expands to include a specific amino acid sequence of SEQ ID NO: 9 or SEQ ID NO: 8. This specification narrows down the scope to particular sequences that may have enhanced affinity or specificity to MSLN.

In embodiments, the intracellular domain of the CAR incorporates a CD3 zeta signaling domain along with one or more co-stimulatory signaling regions selected from a diverse group, which includes CD27, CD28, and 4-1BB, among others. This configuration aims to modulate T-cell activation and potentially increase the therapeutic efficacy of CAR T cell therapy.

The present disclosure relates to a pharmaceutical composition comprising CAR T cells specifically designed for treating a subject diagnosed with MSLN-expressing cancer. These CAR T cells are present in an amount ranging from $1 \times 10^6$ to $1 \times 10^8$ cells per milliliter and are suspended in a pharmaceutically acceptable carrier that includes saline solution and a stabilizing agent. The composition is also noted to be stable for at least 1 month when stored at −80° C., providing practical benefits in terms of storage and distribution.

The present disclosure relates to the use of CAR T cells in the preparation of a medicament specifically intended for treating subjects diagnosed with MSLN-expressing cancers. Administered intravenously, the dosage ranges from $1 \times 10^6$ to $1 \times 10^8$ cells per kilogram of body weight. The treatment is expected to result in a significant reduction in tumor size, set at a threshold of at least 30%.

The present disclosure relates to a method for preparing the pharmaceutical composition described herein. The method involves isolating T cells from a subject, transfecting these cells with a lentiviral vector, culturing the cells under specific conditions, and harvesting them with a purity level of at least 95%.

The present disclosure relates to the use of a pharmaceutical composition in the preparation of a medicament targeted at treating subjects with MSLN-expressing cancers. This composition contains CAR T cells and is prepared using the method outlined above.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples but rather should be construed to encompass any and all variations that become evident as a result of the teaching provided herein.

Examples

The present disclosure is further described by reference to the following examples. These examples are provided for purposes of illustration only and are not intended to be limiting unless otherwise specified. Thus, the present disclosure should in no way be construed as being limited to the following examples but rather should be construed to encompass any and all variations that become evident as a result of the teaching provided herein.

Various nanoantibodies targeting MSLN have been generated. Methods of preparing the nanoantibodies may be found in Bever C S, Dong J X, and Vasylieva N, VHH antibodies: emerging reagents for the analysis of environmental chemicals, Anal Bioanal Chem. 2016; 408(22):5985-6002, doi:10.1007/s00216-016-9585-x; Bao, C., Gao, Q., Li, L.-L., Han, L., Zhang, B., Ding, Y., Song, Z., Zhang, R., Zhang, J., and Wu, X.-H., The Application of Nanobody in CAR-T Therapy. Biomolecules 2021, 11, 238.; and Han, L., Zhang, J S., and Zhou, J., Single VHH-directed BCMA CAR-T cells cause remission of relapsed/refractory multiple myeloma, Leukemia (2021), all of which are incorporated herein by reference in their entirety.

FIGS. 4 to 9 show the results of a series of experiments conducted to assess the binding specificity and affinity of a collection of novel VHH monoclonal antibodies to MSLN, a protein often overexpressed on the surface of certain cancer cells. These experiments involved the staining of 293T control cells and MSLN-positive ASPC-1 cancer cells with various anti-MSLN VHH antibodies. The binding interactions were then measured using flow cytometry, which assesses the fluorescence intensity of the cells after staining, reflecting the antibodies' binding.

In these figures, the histograms from the flow cytometry analysis illustrate two peaks for each sample: one representing the isotype control and the other representing the tested VHH antibody. The fluorescence intensity on the x-axis (FITC B525-FITC-A) indicates the amount of antibody bound, while the y-axis shows the cell count. A rightward shift in the peak of the VHH antibody relative to the isotype control peak suggests specific antibody binding.

Figure 4:
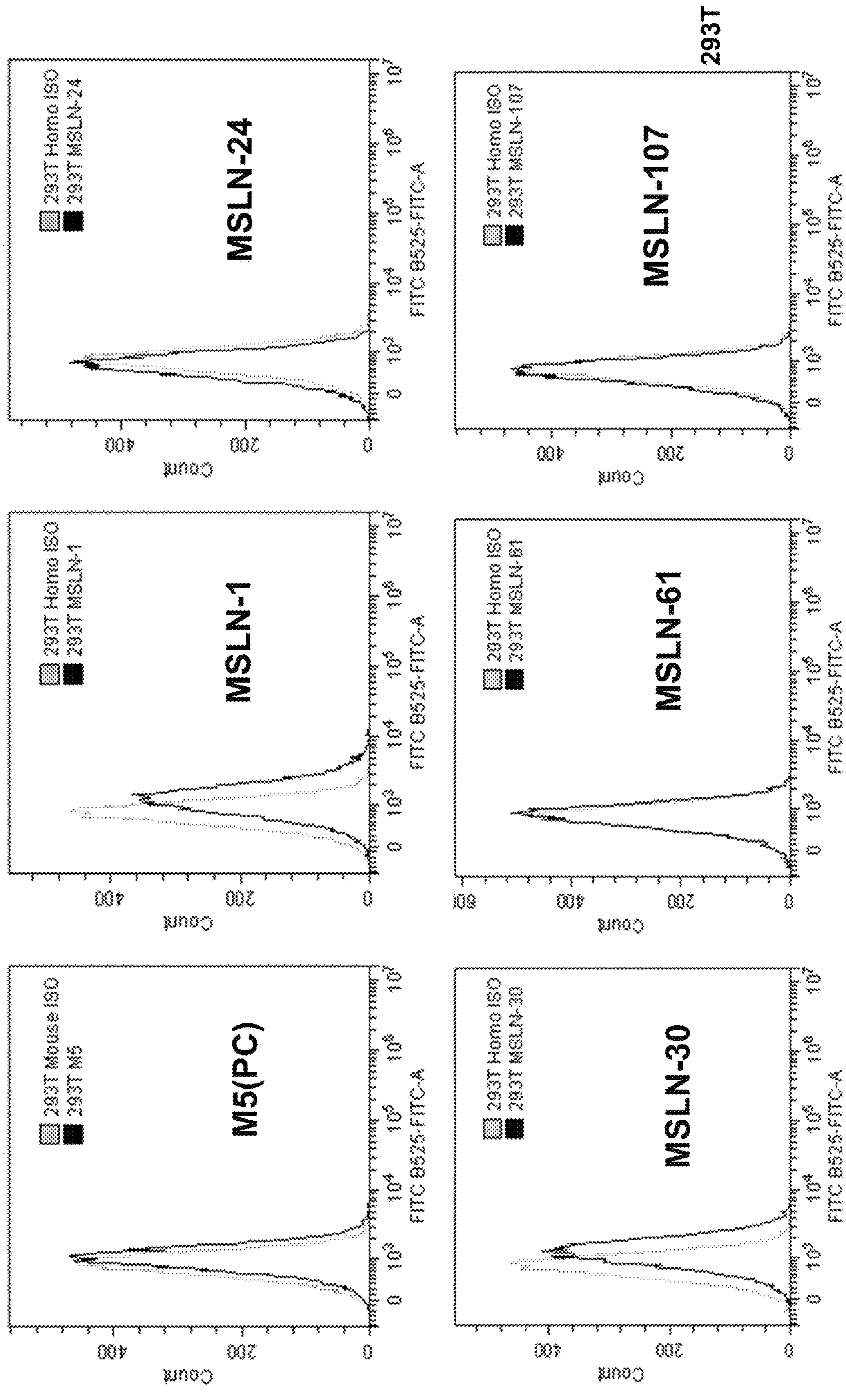
FIGS. 4, 5, 6, 7, 8, and 9 present the results of experiments evaluating the binding specificity and affinity of novel VHH monoclonal antibodies to mesothelin (MSLN), a protein often overexpressed in certain cancer cells, using flow cytometry to quantify the binding interactions.
Figure 5:
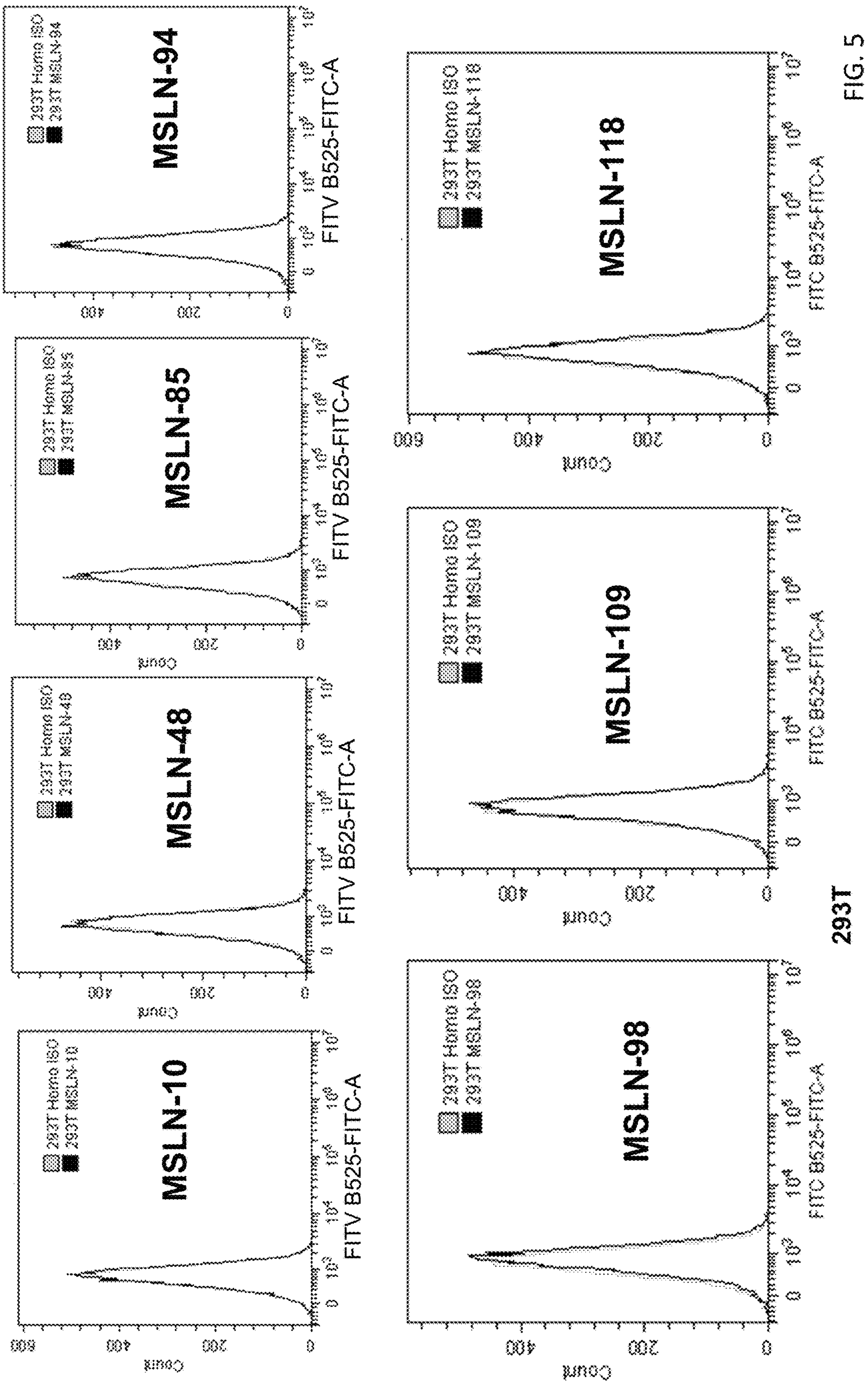
Figure 6:
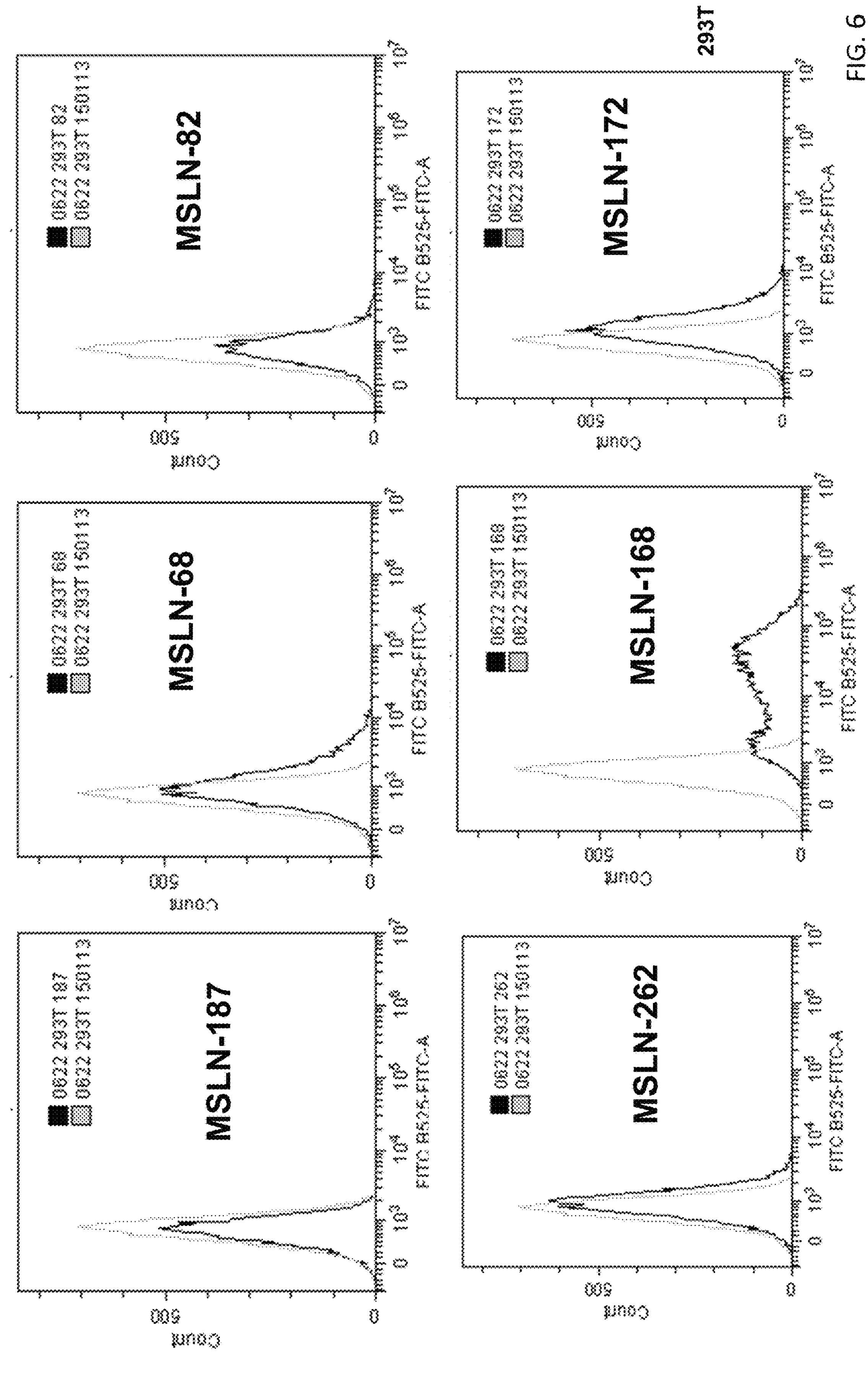
Figure 7:
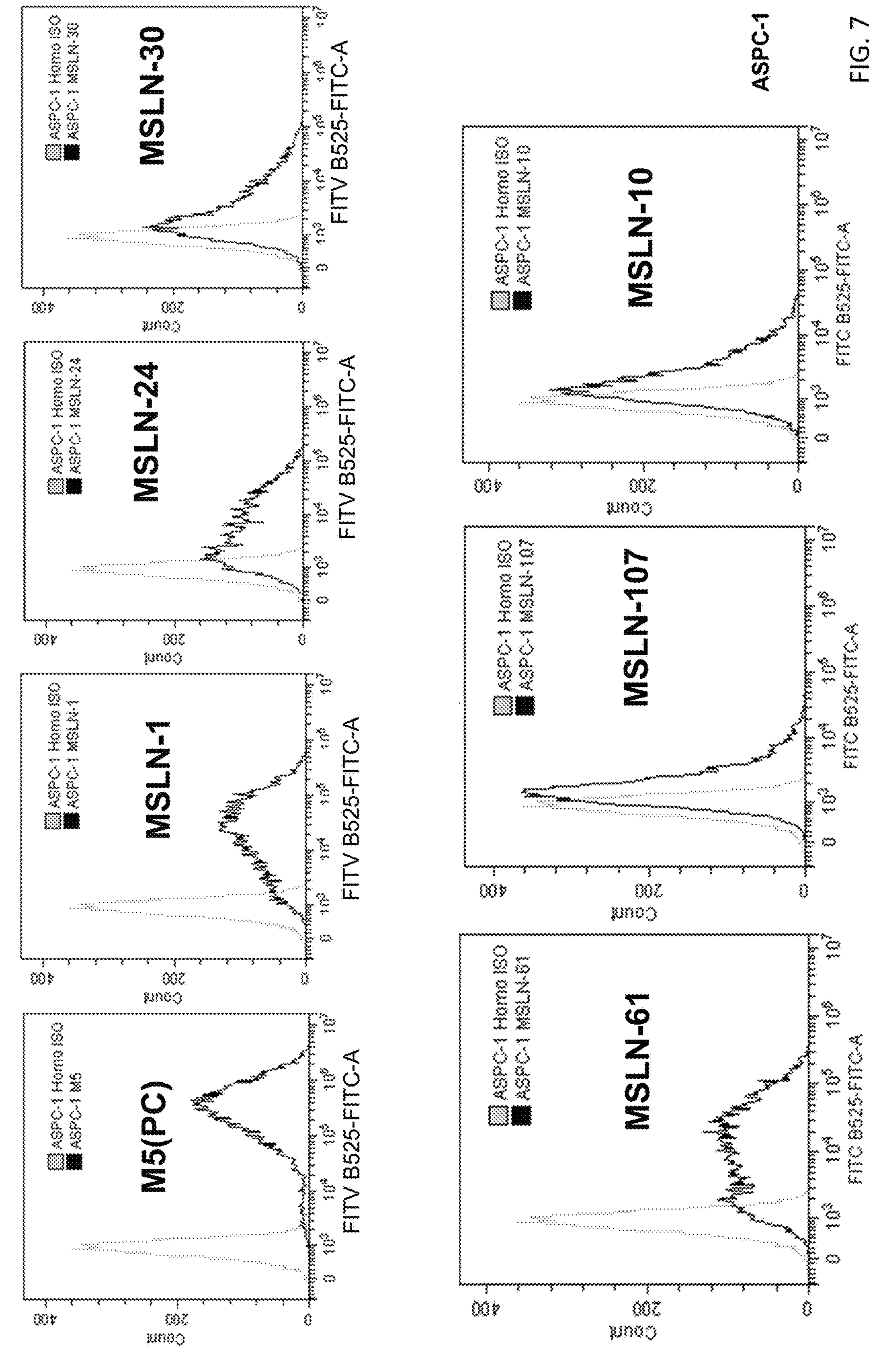
Figure 8:
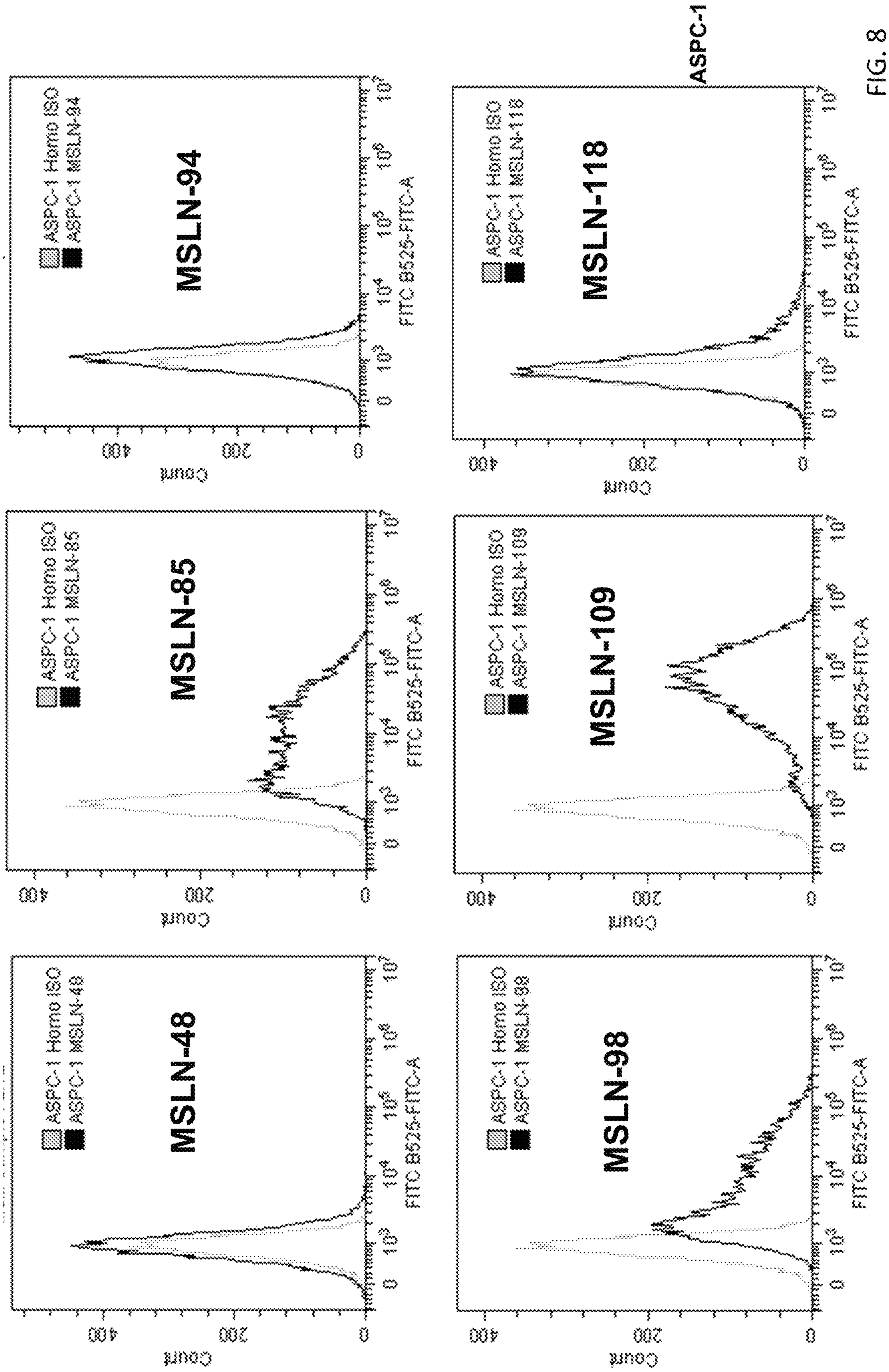
Figure 9:
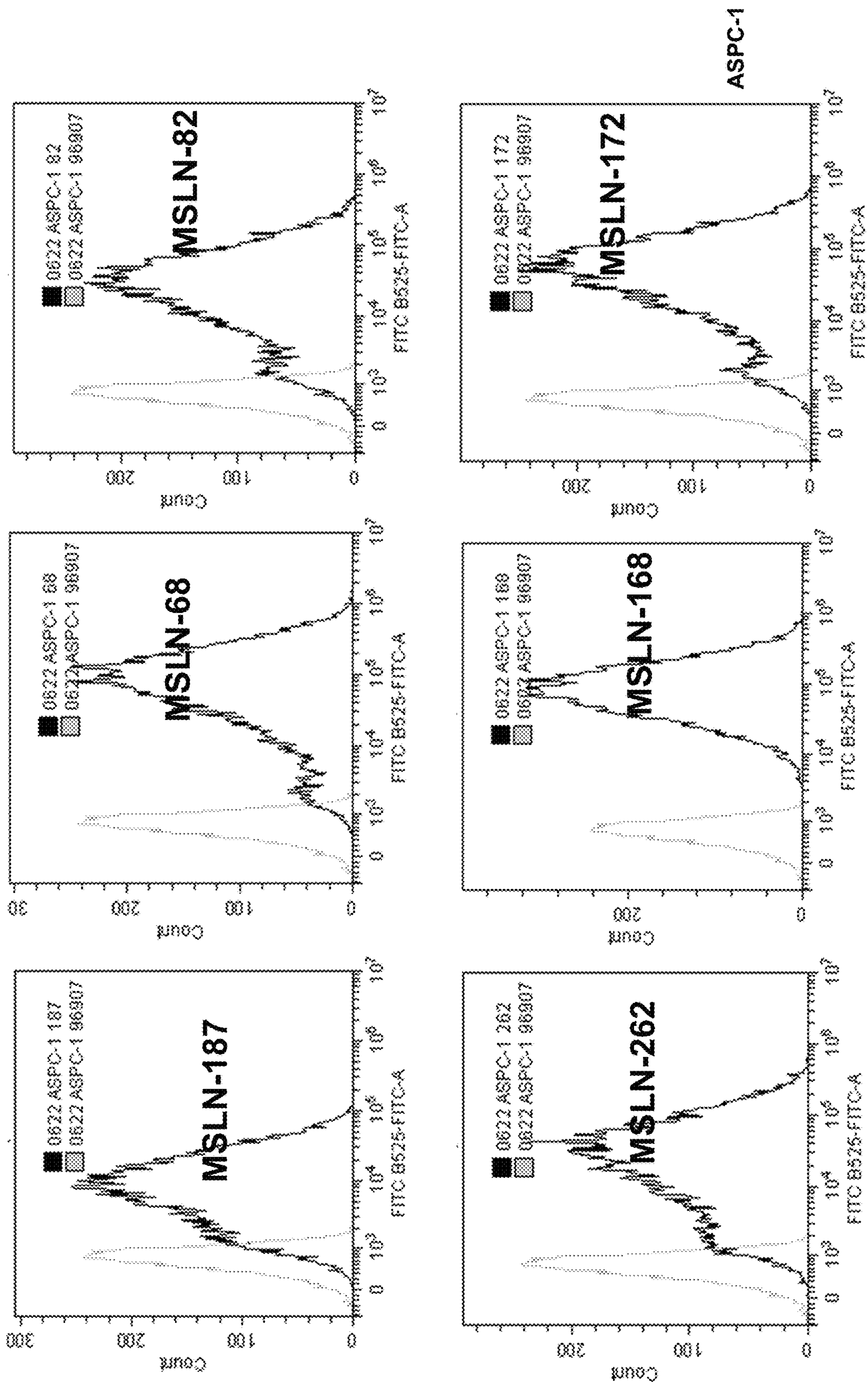

FIGS. 4 to 9 show the results using different anti-MSLN VHH antibodies, identified as MSLN-10, MSLN-48, MSLN-85, MSLN-94, MSLN-98, MSLN-109, MSLN-118, MSLN-187, MSLN-262, MSLN-168, and MSLN-172. FIG. 4 is the first in the series. The control 293T cells typically exhibit a peak corresponding to the isotype control, serving as a baseline for non-specific binding. The MSLN-positive ASPC-1 cells display varying degrees of shift depending on the antibody used, illustrating the differences in binding affinity among the VHH antibodies.

The results across these figures indicate a differential binding capacity of the tested VHH antibodies to the MSLN antigen. Some antibodies exhibit a significant rightward shift, indicating stronger binding to the MSLN antigen, suggesting their utility for therapeutic targeting of MSLN-positive cancer cells. Other antibodies show less pronounced shifts, pointing to lower affinity binding.

These findings indicate that selected VHH antibodies may be suitable for the development of targeted cancer therapies due to their observed binding to MSLN. Together, FIGS. 4 to 9 show the interactions of novel monoclonal antibodies and the MSLN antigen, confirming the potential usefulness of the novel antibodies in cancer diagnosis and treatment.

Table 3 presents the constructs of various CARs. H&TM denotes hinge and transmembrane domain, and BBZ stands for 4-1BB and CD3zeta.

TABLE 3

| # | Constructs |
|---|---|
| 9007 | M5-bbz |
| 9040 | lv-MS1-BBz |
| 9042 | lv-MS24-BBz |
| 9044 | lv-MS61-BBz |
| 9046 | lv-MS85(vl-linker-vh)-CD8 H&TM-4-1BB-CD3z |
| 9048 | lv-MS109(vl-linker-vh)-CD8 H&TM-4-1BB-CD3z |
| 9050 | lv-M2-1 (vl-linker-vh)-CD8 H&TM-4-1BB-CD3z |
| 9051 | lv-M2-30 (vl-linker-vh)-CD8 H&TM-4-1BB-CD3z |
| 9052 | lv-M2-82(vl-linker-vh)-CD8 H&TM-4-1BB-CD3z |
| 9053 | lv-M2-109(vl-linker-vh)-CD8 H&TM-4-1BB-CD3z |
| 9054 | lv-M2-187(vl-linker-vh)-CD8 H&TM-4-1BB-CD3z |

Figure 11:
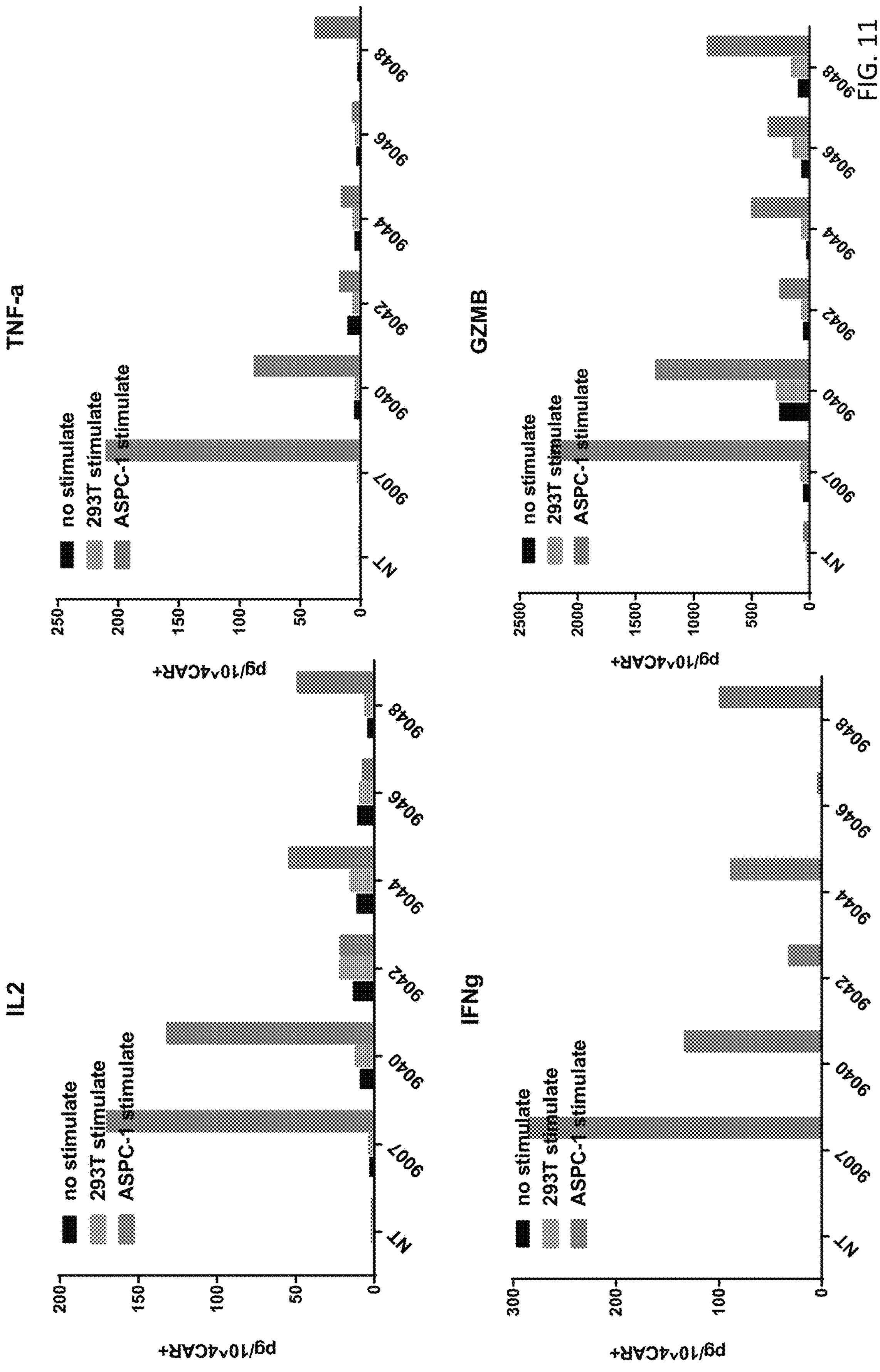
FIGS. 11 and 12 show the results of experiments assessing cytokine secretion by CAR T cells when co-cultured with different cell types, demonstrating an increased secretion of key cytokines upon stimulation with ASPC-1 tumor cells, indicative of the T cells' activation and tumor cell recognition.
Figure 12:
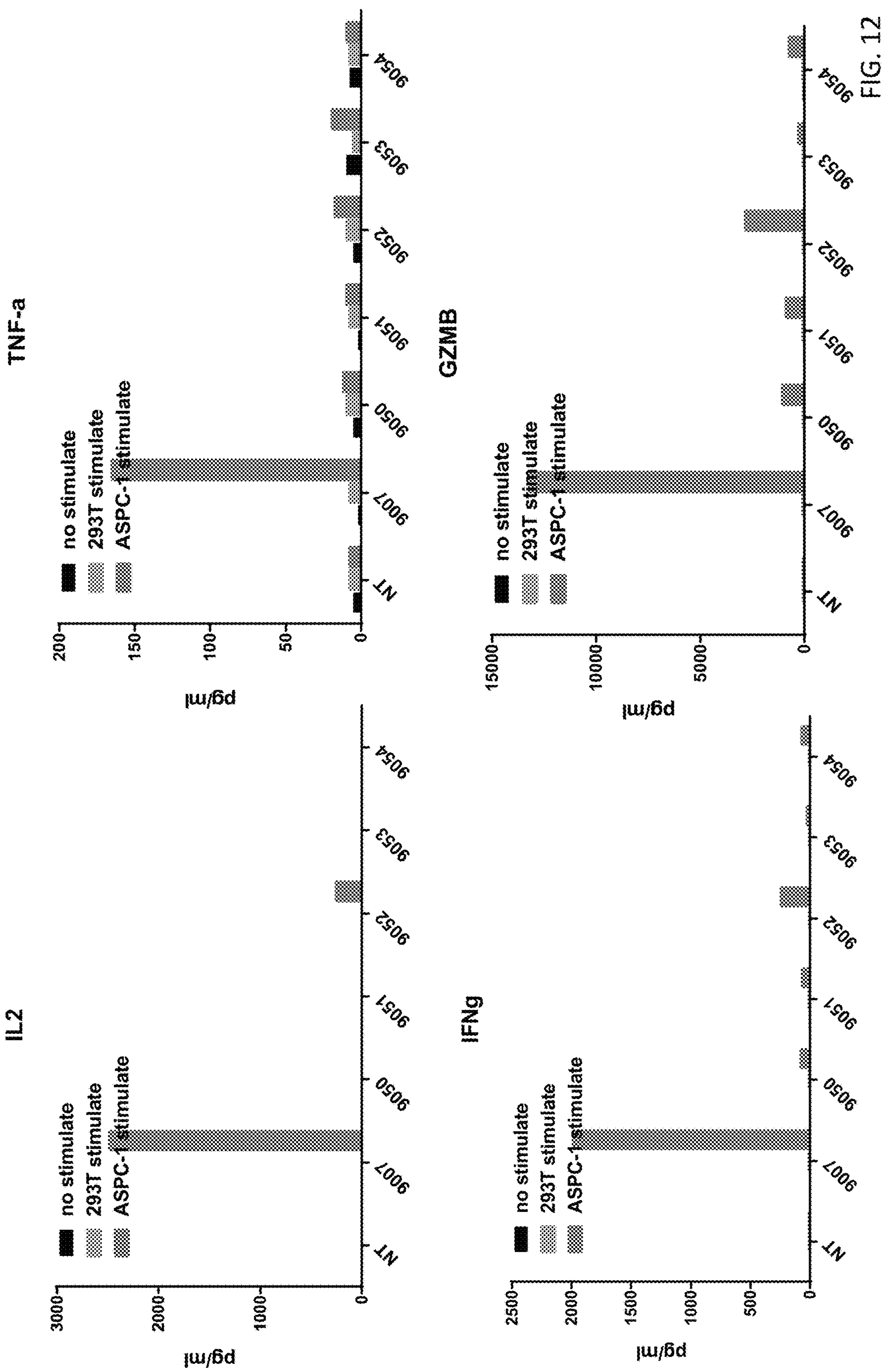

FIGS. 11 and 12 show the results of an experiment aimed at assessing the secretion of various cytokines by chimeric antigen receptor (CAR) T cells upon co-culture with different cell types. The CAR T cells were either left unstimulated, stimulated with 293T cells, or with ASPC-1 tumor cells for 20 hours, and the cytokine secretion was analyzed.

The bar graphs illustrate the production of interleukin-2 (IL-2), tumor necrosis factor-alpha (TNF-α), interferon-gamma (IFNg), and granzyme B (GZMB), which are markers of T cell activation and effector functions. The data indicate that stimulation with ASPC-1 cells leads to increased secretion of these cytokines compared to no stimulation and stimulation with 293T cells, suggesting that the CAR T cells recognize and respond to the ASPC-1 tumor cells.

The noticeable secretion of cytokines in response to ASPC-1 cells affirms the functionality of the CAR construct in recognizing and responding to target tumor antigens. This finding contributes to understanding the potential efficacy of CAR T cells in targeting and eliminating tumor cells. The experiment provides information regarding the reactivity of CAR T cells to different stimuli, which is beneficial for the development and optimization of CAR T cell therapies for cancer treatment.

Figure 10:
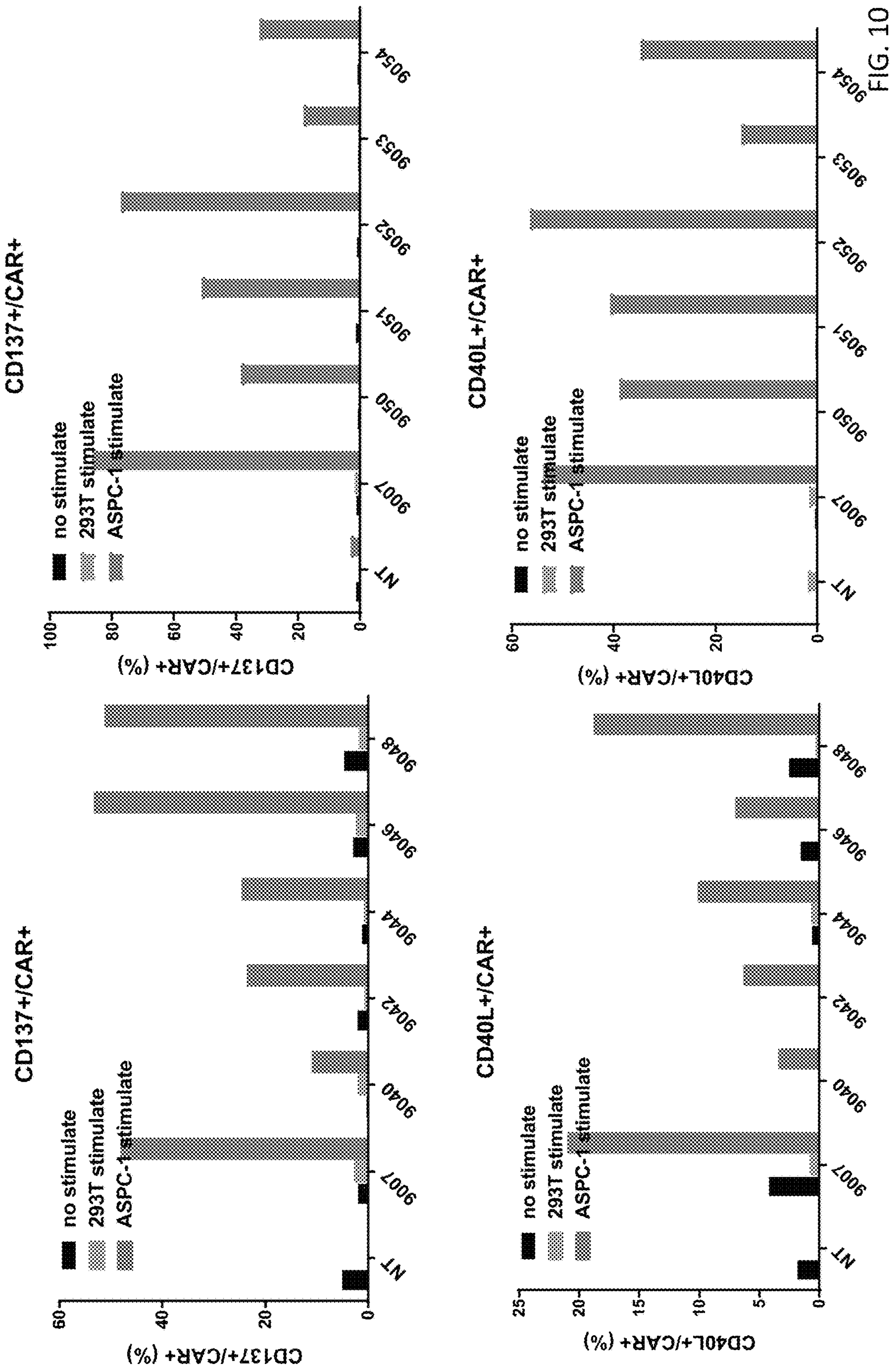
FIG. 10 illustrates the effects of different lentiviral vector constructs on the activation of CAR T cells, showing enhanced activation in response to ASPC-1 tumor cells for specific constructs, thereby demonstrating their functionality in targeting and responding to the presented tumor antigen.

FIG. 10 depicts the results of an experiment exploring the impact of different lentiviral vector constructs on the activation of T cells engineered to express chimeric antigen receptors (CARs). The experiment included exposing these CAR T cells to no stimulus, 293T cells as a negative control, or ASPC-1 cells, which are mesothelin-positive and act as a target for T cell activation. The T cells' response was evaluated by quantifying the secretion of cytokines and expression of activation markers.

The figures demonstrate that the response to the ASPC-1 stimulus was more pronounced for certain constructs, indicating successful activation of the CAR T cells. For instance, in the presence of ASPC-1 cells, the secretion of IL2 and IFNγ was noticeably higher for specific constructs, showing their ability to recognize and respond to the target antigen presented by ASPC-1 cells.

These results indicate that the constructs tested vary in their ability to activate CAR T cells, with some showing strong responses suggesting significant immunotherapeutic potential. The dose-dependent response observed in the presence of ASPC-1 cells supports the specificity of the T cell activation to the target antigen. These findings provide information for manufacturing effective CAR T cell therapies against cancers expressing mesothelin.

Overall, FIGS. 11 and 12 illustrate the specific activation of CAR T cells by various constructs, emphasizing the potential of these engineered T cells in cancer immunotherapy.

TABLE 4

Sequences and Notes

| SEQ ID NO: | CAR references | CAR constructs | Cell references | Type of sequences |
|---|---|---|---|---|
| 1 | 9040 | lv-MS1-BBz | NB311-B-Anti-MSLN-1 | VHH |
| 11 | 9040 | lv-MS1-BBz | NB311-B-Anti-MSLN-1 | CAR |
| 2 | 9042 | lv-MS24-BBz | NB311-B-Anti-MSLN-24 | VHH |
| 12 | 9042 | lv-MS24-BBz | NB311-B-Anti-MSLN-24 | CAR |
| 3 | 9044 | lv-MS61-BBz | NB311-B-Anti-MSLN-61 | VHH |
| 13 | 9044 | lv-MS61-BBz | NB311-B-Anti-MSLN-61 | CAR |
| 4 | 9046 | lv-MS85-BBz | NB311-A-85 | VHH |
| 14 | 9046 | lv-MS85-BBz | NB311-A-85 | CAR |
| 5 | 9048 | lv-MS109-BBz | NB311-B-109 | VHH |
| 15 | 9048 | lv-MS109-BBz | NB311-B-109 | CAR |
| 6 | 9050 | lv-M2-1-BBz | MB311-B-2-1 | VHH |
| 16 | 9050 | lv-M2-1-BBz | MB311-B-2-1 | CAR |
| 7 | 9051 | lv-M2-30-BBz | NB311-A-2-30 | VHH |
| 17 | 9051 | lv-M2-30-BBz | NB311-A-2-30 | CAR |
| 8 | 9052 | lv-M2-82-BBz | NB311-A-2-82 | VHH |
| 18 | 9052 | lv-M2-82-BBz | NB311-A-2-82 | CAR |
| 9 | 9053 | lv-M2-109-BBz | NB311-A-2-109 | VHH |
| 19 | 9053 | lv-M2-109-BBz | NB311-A-2-109 | CAR |
| 10 | 9054 | lv-M2-187-BBz | NB311-B-2-187 | VHH |
| 20 | 9054 | lv-M2-187-BBz | NB311-B-2-187 | CAR |

All publications, patents, and patent applications cited in this specification are incorporated herein by reference in their entirety as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. An antibody that binds mesothelin (MSLN), where in the antibody comprises a VHH domain comprising one of SEQ ID NOs: 1-10.

2. The antibody of claim 1, wherein the antibody comprises SEQ ID NO: 8 or 9.

3. The antibody of claim 1, wherein the antibody is a single domain antibody.

4. The antibody of claim 1, wherein the antibody is conjugated to a cytotoxic agent.

5. The antibody of claim 4, wherein the cytotoxic agent is a radioactive isotope or a toxin.

6. The antibody of claim 1, wherein the antibody is a bispecific antibody comprising the VHH domain, a linker, and an antibody binding CD3.

7. A polynucleotide that encodes the antibody of claim 1.

8. A modified cell comprising the polynucleotide of claim 7.

9. A chimeric antigen receptor (CAR) comprising an extracellular domain comprising the antibody of claim 3.

10. The CAR of claim 9, wherein the CAR comprises a transmembrane domain and an intracellular domain.

11. The CAR of claim 10, wherein the intracellular domain comprises a co-stimulatory signaling region that comprises an intracellular domain of a co-stimulatory molecule comprising at least one of CD27, CD28, 4-1BB, OX40, CD30, CD40, PD-1, ICOS, lymphocyte function-associated antigen-1 (LFA-1), CD2, CD7, LIGHT, NKG2C, and B7-H3.

12. The CAR of claim 9, wherein the CAR comprises one of SEQ ID NO: 11-20.

13. A polynucleotide that encodes the CAR of claim 9.

14. A modified cell comprising the polynucleotide of claim 13.

15. The modified cell of claim 14, wherein the modified cell is a T cell or NK cell.

16. A composition comprising a population of the modified cells of claim 14.

17. The composition of claim 16, wherein the modified cells have reduced expression of endogenous T cell receptor alpha constant (TRAC) gene.

18. The composition of claim 16, wherein the modified cells comprise a polynucleotide encoding hTERT, a nucleic acid encoding SV40LT, or a combination thereof.

19. The composition of claim 16, wherein the modified cells comprise a polynucleotide encoding a cytokine.

20. The composition of claim 16, wherein the CAR comprises one of SEQ ID NO: 11-20.

21. The composition of claim 16, wherein the modified cells comprise a polynucleotide encoding at least one of IL-6, IFNγ, IL-12, and IL-2.

* * * * *

SEQUENCE LISTING

```
Sequence total quantity: 20
SEQ ID NO: 1            moltype = AA  length = 117
FEATURE                 Location/Qualifiers
source                  1..117
                        mol_type = protein
                        organism = synthetic construct
SEQUENCE: 1
EVQVVESGGG LVHPGGSLSL SCAASGSIFS IDVMAWYRQA PGKQRELVAS IARTGSTDYA  60
DSVKGRFTIS RNNAGDTLYL QMNSLKPEDT AFYSCHAISL RPPRQYWGRG TQVTVNS     117

SEQ ID NO: 2            moltype = AA  length = 133
FEATURE                 Location/Qualifiers
source                  1..133
                        mol_type = protein
                        organism = synthetic construct
SEQUENCE: 2
EVQLVESGGG LVQAGGSLRL SCAASGNIPS LNVMGWYRQA PGKQRELVAS VASSGTTHLE  60
DSVKGRFTIS KDNAKNTMYL QMNSLKPEDT AVYYCVLVDV SALPGGRLDY WGQGTPRGRL  120
DYWGQGTQVT VSS                                                     133
```

```
SEQ ID NO: 3            moltype = AA  length = 117
FEATURE                 Location/Qualifiers
source                  1..117
                        mol_type = protein
                        organism = synthetic construct
SEQUENCE: 3
EVQVVESGGG LVQAGGSLRL SCAASGSIFR INVMAWYRII PEKQRELVAS IATTGTTDYA  60
DSVKGRFTIS RDNAQNTMLL QMNSLKPEDT AVYYCYLHDL RDGNGYWGQG TQVTVSS     117

SEQ ID NO: 4            moltype = AA  length = 132
FEATURE                 Location/Qualifiers
source                  1..132
                        mol_type = protein
                        organism = synthetic construct
SEQUENCE: 4
QLQLVESGGG LVQPGGSLRL SCVASGIFNP NVMAWYRQAP GKQRELVASV ASSGTTHYED  60
SVKGRFTISK DNAKNTMYLQ MNSLKPEDTA VYYCILVDVS ALPGGRLDYW GQGTPRGRLD  120
YWGQGTQVTV SS                                                      132

SEQ ID NO: 5            moltype = AA  length = 114
FEATURE                 Location/Qualifiers
source                  1..114
                        mol_type = protein
                        organism = synthetic construct
SEQUENCE: 5
EVQVVESGGG SVPAGGSLRL SCVWSGITAR RNIMRWYRQA PGKQREWIAS VYADFTTGYD  60
DSVSGRFTVS RDNAKNTAYL QMDALKPEDT AVYYCNSQTA PQVWGQGTQV IVSS        114

SEQ ID NO: 6            moltype = AA  length = 125
FEATURE                 Location/Qualifiers
source                  1..125
                        mol_type = protein
                        organism = synthetic construct
SEQUENCE: 6
EVQVVESGGG LVQAGGSLRL SCAASGRTDN MYATGWLRQA PGKEREFVAI ISWGGGTTRY  60
ADPVKGRFTI SRDYTKRTVY LQMNSLKPED TAVYYCATVV TKVVDGQEID DYSSLGQGTQ  120
VTVSS                                                              125

SEQ ID NO: 7            moltype = AA  length = 117
FEATURE                 Location/Qualifiers
source                  1..117
                        mol_type = protein
                        organism = synthetic construct
SEQUENCE: 7
QVQLVESGGG LVHPGGSLSL SCAASGSIFS IDVTGWYRQA PGKQRELVAS IARTGTTDYA  60
DSVKGRFTIS RNNAGDAVYL QMNSLKPEDT AFYSCHAVSL HPPRQYWGRG TQVTVNS     117

SEQ ID NO: 8            moltype = AA  length = 117
FEATURE                 Location/Qualifiers
source                  1..117
                        mol_type = protein
                        organism = synthetic construct
SEQUENCE: 8
EVQVVESGGG LVQAGGSLRL SCIASGNIAS KNIMAWYRQA PGKQRELVAS ISSVLTTYIA  60
PSVKGRFTIS RDNAKNTMYL EMTSLIPEDT AKYFCNFLEY PSTTNYFGQG TQVTVSS     117

SEQ ID NO: 9            moltype = AA  length = 118
FEATURE                 Location/Qualifiers
source                  1..118
                        mol_type = protein
                        organism = synthetic construct
SEQUENCE: 9
EVQVVESGGG LVQAGGSLRL SCVVSESMRL TIMAWYRLAP GKERELVASI SDFATAYGDS  60
VKGRFTISRD NPKKTMFLHM NNLKPTDTAV YYCYGRTGFL EPGVEEYWGQ GTQVTVSS    118

SEQ ID NO: 10           moltype = AA  length = 125
FEATURE                 Location/Qualifiers
source                  1..125
                        mol_type = protein
                        organism = synthetic construct
SEQUENCE: 10
EVQVVESGGG LVQAGGSLRL SCAASGRTDN MYATGWLRQA PGKEREFVAI ISWGGGTTRY  60
ADPVKGRFVI SRDHTKNTVY LQMNSLKPED TGVYYCVTVV SKVVAGQEID DYSSWGQGTQ  120
VTVSS                                                              125

SEQ ID NO: 11           moltype = AA  length = 493
FEATURE                 Location/Qualifiers
source                  1..493
                        mol_type = protein
```

```
                         organism = synthetic construct
SEQUENCE: 11
MALPVTALLL PLALLLHAAR PEVQVVESGG GLVHPGGSLS LSCAASGSIF SIDVMAWYRQ  60
APGKQRELVA SIARTGSTDY ADSVKGRFTI SRNNAGDTLY LQMNSLKPED TAFYSCHAIS  120
LRPPRQYWGR GTQVTVNSGG GGSGGGGSGG GGSEVQVVES GGGLVHPGGS LSLSCAASGS  180
IFSIDVMAWY RQAPGKQREL VASIARTGST DYADSVKGRF TISRNNAGDT LYLQMNSLKP  240
EDTAFYSCHA ISLRPPRQYW GRGTQVTVNS TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 12            moltype = AA  length = 525
FEATURE                  Location/Qualifiers
source                   1..525
                         mol_type = protein
                         organism = synthetic construct
SEQUENCE: 12
MALPVTALLL PLALLLHAAR PEVQLVESGG GLVQAGGSLR LSCAASGNIP SLNVMGWYRQ  60
APGKQRELVA SVASSGTTHL EDSVKGRFTI SKDNAKNTMY LQMNSLKPED TAVYYCVLVD  120
VSALPGGRLD YWGQGTPRGR LDYWGQGTQV TVSSGGGGSG GGGSGGGGSE VQLVESGGGL  180
VQAGGSLRLS CAASGNIPSL NVMGWYRQAP GKQRELVASV ASSGTTHLED SVKGRFTISK  240
DNAKNTMYLQ MNSLKPEDTA VYYCVLVDVS ALPGGRLDYW GQGTPRGRLD YWGQGTQVTV  300
SSTTTPAPRP PTPAPTIASQ PLSLRPEACR PAAGGAVHTR GLDFACDIYI WAPLAGTCGV  360
LLLSLVITLY CKRGRKKLLY IFKQPFMRPV QTTQEEDGCS CRFPEEEEGG CELRVKFSRS  420
ADAPAYQQGQ NQLYNELNLG RREEYDVLDK RRGRDPEMGG KPRRKNPQEG LYNELQKDKM  480
AEAYSEIGMK GERRRGKGHD GLYQGLSTAT KDTYDALHMQ ALPPR                 525

SEQ ID NO: 13            moltype = AA  length = 493
FEATURE                  Location/Qualifiers
source                   1..493
                         mol_type = protein
                         organism = synthetic construct
SEQUENCE: 13
MALPVTALLL PLALLLHAAR PEVQVVESGG GLVQAGGSLR LSCAASGSIF RINVMAWYRI  60
IPEKQRELVA SIATTGTTDY ADSVKGRFTI SRDNAQNTML LQMNSLKPED TAVYYCYLHD  120
LRDGNGYWGQ GTQVTVSSGG GGSGGGGSGG GGSEVQVVES GGGLVQAGGS LRLSCAASGS  180
IFRINVMAWY RIIPEKQREL VASIATTGTT DYADSVKGRF TISRDNAQNT MLLQMNSLKP  240
EDTAVYYCYL HDLRDGNGYW GQGTQVTVSS TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 14            moltype = AA  length = 523
FEATURE                  Location/Qualifiers
source                   1..523
                         mol_type = protein
                         organism = synthetic construct
SEQUENCE: 14
MALPVTALLL PLALLLHAAR PQLQLVESGG GLVQPGGSLR LSCVASGIFN PNVMAWYRQA  60
PGKQRELVAS VASSGTTHYE DSVKGRFTIS KDNAKNTMYL QMNSLKPEDT AVYYCILVDV  120
SALPGGRLDY WGQGTPRGRL DYWGQGTQVT VSSGGGGSGG GGSGGGGSQL QLVESGGGLV  180
QPGGSLRLSC VASGIFNPNV MAWYRQAPGK QRELVASVAS SGTTHYEDSV KGRFTISKDN  240
AKNTMYLQMN SLKPEDTAVY YCILVDVSAL PGGRLDYWGQ GTPRGRLDYW GQGTQVTVSS  300
TTTPAPRPPT PAPTIASQPL SLRPEACRPA AGGAVHTRGL DFACDIYIWA PLAGTCGVLL  360
LSLVITLYCK RGRKKLLYIF KQPFMRPVQT TQEEDGCSCR FPEEEEGGCE LRVKFSRSAD  420
APAYQQGQNQ LYNELNLGRR EEYDVLDKRR GRDPEMGGKP RRKNPQEGLY NELQKDKMAE  480
AYSEIGMKGE RRRGKGHDGL YQGLSTATKD TYDALHMQAL PPR                   523

SEQ ID NO: 15            moltype = AA  length = 487
FEATURE                  Location/Qualifiers
source                   1..487
                         mol_type = protein
                         organism = synthetic construct
SEQUENCE: 15
MALPVTALLL PLALLLHAAR PEVQVVESGG GSVPAGGSLR LSCVWSGITA RRNIMRWYRQ  60
APGKQREWIA SVYADFTTGY DDSVSGRFTV SRDNAKNTAY LQMDALKPED TAVYYCNSQT  120
APQVWGQGTQ VIVSSGGGGS GGGGSGGGGS EVQVVESGGG SVPAGGSLRL SCVWSGITAR  180
RNIMRWYRQA PGKQREWIAS VYADFTTGYD DSVSGRFTVS RDNAKNTAYL QMDALKPEDT  240
AVYYCNSQTA PQVWGQGTQV IVSSTTTPAP RPPTPAPTIA SQPLSLRPEA CRPAAGGAVH  300
TRGLDFACDI YIWAPLAGTC GVLLLSLVIT LYCKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                           487

SEQ ID NO: 16            moltype = AA  length = 509
FEATURE                  Location/Qualifiers
source                   1..509
```

```
                        mol_type = protein
                        organism = synthetic construct
SEQUENCE: 16
MALPVTALLL PLALLLHAAR PEVQVVESGG GLVQAGGSLR LSCAASGRTD NMYATGWLRQ  60
APGKEREFVA IISWGGGTTR YADPVKGRFT ISRDYTKRTV YLQMNSLKPE DTAVYYCATV  120
VTKVVDGQEI DDYSSLGQGT QVTVSSGGGG SGGGGSGGGG SEVQVVESGG GLVQAGGSLR  180
LSCAASGRTD NMYATGWLRQ APGKEREFVA IISWGGGTTR YADPVKGRFT ISRDYTKRTV  240
YLQMNSLKPE DTAVYYCATV VTKVVDGQEI DDYSSLGQGT QVTVSSTTTP APRPPTPAPT  300
IASQPLSLRP EACRPAAGGA VHTRGLDFAC DIYIWAPLAG TCGVLLLSLV ITLYCKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                    509

SEQ ID NO: 17           moltype = AA  length = 493
FEATURE                 Location/Qualifiers
source                  1..493
                        mol_type = protein
                        organism = synthetic construct
SEQUENCE: 17
MALPVTALLL PLALLLHAAR PQVQLVESGG GLVHPGGSLS LSCAASGSIF SIDVTGWYRQ  60
APGKQRELVA SIARTGTTDY ADSVKGRFTI SRNNAGDAVY LQMNSLKPED TAFYSCHAVS  120
LHPPRQYWGR GTQVTVNSGG GGSGGGGSGG GGSQVQLVES GGGLVHPGGS LSLSCAASGS  180
IFSIDVTGWY RQAPGKQREL VASIARTGTT DYADSVKGRF TISRNNAGDA VYLQMNSLKP  240
EDTAFYSCHA VSLHPPRQYW GRGTQVTVNS TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                     493

SEQ ID NO: 18           moltype = AA  length = 493
FEATURE                 Location/Qualifiers
source                  1..493
                        mol_type = protein
                        organism = synthetic construct
SEQUENCE: 18
MALPVTALLL PLALLLHAAR PEVQVVESGG GLVQAGGSLR LSCIASGNIA SKNIMAWYRQ  60
APGKQRELVA SISSVLTTYI APSVKGRFTI SRDNAKNTMY LEMTSLIPED TAKYFCNFLE  120
YPSTTNYFGQ GTQVTVSSGG GGSGGGGSGG GGSEVQVVES GGGLVQAGGS LRLSCIASGN  180
IASKNIMAWY RQAPGKQREL VASISSVLTT YIAPSVKGRF TISRDNAKNT MYLEMTSLIP  240
EDTAKYFCNF LEYPSTTNYF GQGTQVTVSS TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                     493

SEQ ID NO: 19           moltype = AA  length = 495
FEATURE                 Location/Qualifiers
source                  1..495
                        mol_type = protein
                        organism = synthetic construct
SEQUENCE: 19
MALPVTALLL PLALLLHAAR PEVQVVESGG GLVQAGGSLR LSCVVSESMR LTIMAWYRLA  60
PGKERELVAS ISDFATAYGD SVKGRFTISR DNPKKTMFLH MNNLKPTDTA VYYCYGRTGF  120
LEPGVEEYWG QGTQVTVSSG GGGSGGGGSG GGGSEVQVVE SGGGLVQAGG SLRLSCVVSE  180
SMRLTIMAWY RLAPGKEREL VASISDFATA YGDSVKGRFT ISRDNPKKTM FLHMNNLKPT  240
DTAVYYCYGR TGFLEPGVEE YWGQGTQVTV SSTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 20           moltype = AA  length = 509
FEATURE                 Location/Qualifiers
source                  1..509
                        mol_type = protein
                        organism = synthetic construct
SEQUENCE: 20
MALPVTALLL PLALLLHAAR PEVQVVESGG GLVQAGGSLR LSCAASGRTD NMYATGWLRQ  60
APGKEREFVA IISWGGGTTR YADPVKGRFV ISRDHTKNTV YLQMNSLKPE DTGVYYCVTV  120
VSKVVAGQEI DDYSSWGQGT QVTVSSGGGG SGGGGSGGGG SEVQVVESGG GLVQAGGSLR  180
LSCAASGRTD NMYATGWLRQ APGKEREFVA IISWGGGTTR YADPVKGRFV ISRDHTKNTV  240
YLQMNSLKPE DTGVYYCVTV VSKVVAGQEI DDYSSWGQGT QVTVSSTTTP APRPPTPAPT  300
IASQPLSLRP EACRPAAGGA VHTRGLDFAC DIYIWAPLAG TCGVLLLSLV ITLYCKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                    509
```